(12) United States Patent
Krauss et al.

(10) Patent No.: US 9,857,385 B2
(45) Date of Patent: Jan. 2, 2018

(54) ULTRA-SMALL APOB-CONTAINING PARTICLES AND METHODS OF USE THEREOF

(71) Applicant: Children's Hospital & Research Center at Oakland, Oakland, CA (US)

(72) Inventors: Ronald M. Krauss, Berkeley, CA (US); Mohmed Elfatih Ashmaig, Richmond, VA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 0 days.

(21) Appl. No.: 15/137,705

(22) Filed: Apr. 25, 2016

(65) Prior Publication Data

US 2016/0231340 A1    Aug. 11, 2016

Related U.S. Application Data

(63) Continuation of application No. 14/123,927, filed as application No. PCT/US2012/042513 on Jun. 14, 2012, now Pat. No. 9,322,833.

(60) Provisional application No. 61/497,847, filed on Jun. 16, 2011.

(51) Int. Cl.
| | |
|---|---|
| C07K 14/775 | (2006.01) |
| G01N 33/92 | (2006.01) |
| C07K 14/47 | (2006.01) |
| B82Y 15/00 | (2011.01) |
| G01N 33/68 | (2006.01) |
| B82Y 5/00 | (2011.01) |

(52) U.S. Cl.
CPC .............. *G01N 33/92* (2013.01); *B82Y 15/00* (2013.01); *C07K 14/4741* (2013.01); *C07K 14/775* (2013.01); *G01N 33/6887* (2013.01); *G01N 33/6893* (2013.01); *B82Y 5/00* (2013.01); *G01N 2333/4742* (2013.01); *G01N 2333/775* (2013.01); *G01N 2800/32* (2013.01); *G01N 2800/52* (2013.01); *Y10T 428/2982* (2015.01)

(58) Field of Classification Search
CPC .............................. C07K 14/775; G01N 33/92
See application file for complete search history.

(56) References Cited

U.S. PATENT DOCUMENTS

| | | | |
|---|---|---|---|
| 5,925,229 A | 7/1999 | Krauss et al. | |
| 7,259,018 B2 | 8/2007 | Benner et al. | |
| 7,713,744 B2 | 5/2010 | Benner et al. | |
| 2002/0177240 A1* | 11/2002 | Kundu | C07K 16/18 436/514 |
| 2003/0096316 A1* | 5/2003 | Wester | G01N 33/92 435/7.2 |
| 2003/0124743 A1* | 7/2003 | Kundu | C07K 16/18 436/518 |
| 2006/0177435 A1* | 8/2006 | Tsimikas | G01N 33/92 424/133.1 |
| 2008/0038829 A1 | 2/2008 | Kremer et al. | |
| 2009/0132443 A1* | 5/2009 | Mueller | G06F 19/18 706/12 |
| 2009/0317819 A1 | 12/2009 | Tsimikas et al. | |
| 2010/0035983 A1* | 2/2010 | Shiffman | C12Q 1/6883 514/510 |
| 2010/0183607 A1* | 7/2010 | Hazen | G01N 33/6893 424/133.1 |
| 2010/0213061 A1* | 8/2010 | Benner | G01N 15/0266 204/450 |
| 2010/0323376 A1 | 12/2010 | Contois | |

OTHER PUBLICATIONS

Shin et al., 2010, Apolipoprotein CIII bound apoB-containing lipoproteins is associated with small, dense LDL independent of plasma triglyceride levels in healthy men, Atherosclerosis, 211: 337-341.*
Steer et al., 2002, Endothelial Vasodilatory Function Is Predicted by Circulating Apolipoprotein B and HDL in Healthy Humans, Lipids, 37(12): 1135-1140.*
Marcoux et al., 1999, Characterization of remnant-like particles isolated by immunoaffinity gel from the plasma of type III and type IV hyperlipoproteinemic patients, Journal of Lipid Research, 40: 636-647.*
Vezina et al., 1988, Apolipoprotein distribution in human lipoproteins separated by polyacrylamide gradient gel electrophoresis, Journal of Lipid Research, 29: 573-585.*
Lau et al., 2009, Advanced Lipoprotein Testing: Recommendations Based on Current Evidence, Endocrinol Metab Clin N Am, 38: 1-31.*
Nakano et al., 2008, Detection of apolipoproteins B-48 and B-100 carrying particles in lipoprotein fractions extracted from human aortic atherosclerotic plaques in sudden cardiac death cases, Clinica Chimica Acta, 390: 38-43.*
Stakisaitis et al., 2004, Blood serum apolipoproteins B and A-I in females suffering from rheumatic heart valve disease, Medicina, 40(1): 33-37.*
Zhang et al., 2005, Correlation of high density lipoprotein (HDL)-associated sphingosine 1-phosphate with serum levels of HDL-cholesterol and apolipoproteins, Atherosclerosis, 178: 199-205.*
Vekic et al., Small, dense LDL cholesterol and apolipoprotein B: Relationship with serum lipids and LDL size, Atherosclerosis, 207: 496-501.*
Al-Bahrani, et al.; "A potential role of apolipoprotein B in the risk stratification of diabetic patients with dyslipidaemia"; Diabetes Research and Clinical Practice; vol. 69, No. 1, pp. 44-51 (Jul. 2005).

(Continued)

*Primary Examiner* — Amber D Steele
(74) *Attorney, Agent, or Firm* — Bozicevic Field & Francis, LLP; Paula A. Borden

(57) ABSTRACT

The present disclosure provides an isolated particle comprising very high density, ultra small, lipid depleted apo B containing particles, and may also contain cytokeratin 8. The isolated particle is useful in diagnostic assays, which are also provided.

27 Claims, 16 Drawing Sheets

(56) References Cited

OTHER PUBLICATIONS

Katsuda, et al.; "Human Atherosclerosis: Immunocytochemical Analysis of the Cell Composition of Lesions of Young Adults"; American Journal of Pathology; vol. 140, No. 4, pp. 907-914 (Apr. 1992).
Koba, et al.; "Significance of small dense low-density lipoproteins and other risk factors in patients with various types of coronary heart disease"; Am. Heart. J.; vol. 144, No. 6, pp. 1026-1035 (2002).
Ogasawara, et al; "Low-density lipoprotein (LDL), which includes apolipoprotein A-I (apoAI-LDL) as a novel marker of coronary artery disease"; Clinica Chimica Acta; vol. 397, pp. 42-47 (2008).

\* cited by examiner apoB-100
GenBank NP_000375.2

```
   1 mdpprpalla llalpallll llagaraeee mlenvslvcp kdatrfkhlr kytynyeaes
  61 ssgvpgtads rsatrinckv elevpqlcsf ilktsqctlk evygfnpegk allkktknse
 121 efaaamsrye lklaipegkq vflypekdep tyilnikrgi isallvppet eeakqvlfld
 181 tvygncsthf tvktrkgnva teisterdlg qcdrfkpirt gispla-ikg mtrplstlis
 241 ssqscqytld akrkhvaeai ckeqhlflpf syknkygmva qvtqtlkled tpkinsrffg
 301 egtkkmglaf estkstsppk qaeavlktlq elkkltiseq niqran-fnk lvtelrglsd
 361 eavtsllpql ievsspitlq alvqcgqpqc sthilqwlkr vhanpllidv vtylvalipe
 421 psaggreif nmardqrsra tlyalshavn nyhktnptgt qelldianyl meqiqddctg
 481 dedytylilr vignmgqtme qltpelkssi lkcvqstkps lmiqkaaiqa lrkmepkdkd
 541 qevllqtfld daspgdkrla aylmlmrsps qadinkivqi lpweqneqvk nfvashiani
 601 lnseeldiqd lkklvkealk esqlptvmdf rkfsrnyqly ksvslpsldp asakiegnli
 661 fdpnnylpke smlkttltaf gfasadliei glegkgfept lealfgkqgf fpdsvnkaly
 721 wvngqvpdgv skvlvdhfgy tkddkheqdm vngimlsvek likdlkskev pearaylril
 781 geelgfaslh dlqllgklll mgartlqgip mgartlqgip qmigevirkg skndff-hyi fmenafelpt
 841 gaglqlqiss sgviapyaka gvklevanmq aelvakpsvs vefvtnrngii ipdfarsgvq
 901 mntnffhesg leahvalkag klkfliipspk rpvkllsggn tlhlvsttkt evipplienr
 961 qswsvckqvf pglnyctsga ysnasstdsa syypltgdtr lelelrptge ieqysvsaty
1021 elqredralv dtlkfvtqae gakqteatmt fknyrqsmtl ssevqipdfd vdlgtilrvn
1081 destegktsy rltldiqnkk itevalmghl scdtkeerki kgvisiprlq aearseilah
1141 wspakllqm dssataygst vskrvawhyd eekiefewnt gtnvdtkkmt snfpvdlsdy
```

FIG. 17A

```
1201  pkslhmyanr  lldhrvpqtd  mtfrhvgskl  ivamsswlqk  asgslpytqt  lqdhlnslke
1261  fnlqnmglpd  fhipenlflk  sdgrvkytln  knslkieipl  pfggkssrdl  kmletvrtpa
1321  lhfksvgfhl  psrefqvptf  tipklyqlqv  pllgvldlst  nvysnlynws  asysggntst
1381  dhfslraryh  mkadsvvdll  synvqgsget  tydhkntftl  scdgslrhkf  ldsnikfshv
1441  eklgnnpvsk  gllifdasss  wgpqmsasvh  ldskkkqhlf  vkevkidgqf  rvssfyakgt
1501  yglscqrdpn  tgrlngesnl  rfnssylqgt  nqitgryedg  tlsltstsdl  qsgiikntas
1561  lkyenyeltl  ksdtngkykn  fatsnkmdmt  fskqnallrs  eyqadyeslr  ffsllsgsln
1621  shglelnadi  lgtdkinsga  hkatlriggd  gistsattnl  kcsllvlene  lnaelglsga
1681  smklttngrf  rehnakfsld  gkaaltelsl  gsayqamilg  vdsknifnfk  vsqeglklsn
1741  dmmgsyaemk  fdhtnslnia  glsldfsskl  dniyssdkfy  kqtvnlqlqp  yslvttlnsd
1801  lkynaldltn  ngklrleplk  lhvagnlkga  yqnneikhiy  aissaalsas  ykadtvakvq
1861  gvefshrlnt  diaglasaid  mstnynsdsl  hfsnvfrsvm  apftmtidah  tngngklalw
1921  gehtgqlysk  fllkaeplaf  tfshdykgst  shhlvsrksi  saalehkvsa  lltpaeqtgt
1981  wklktqfnnn  eysqdldayn  tkdkigvelt  grtladltll  dspikvplll  sepiniidal
2041  emrdavekpq  eftivafvky  dknqdvhsin  lpffetlqey  fernrqtiiv  vlenvqrnlk
2101  hinidqfvrk  yraalgklpq  qandylnsfn  werqvshake  kltaltkkyr  itendiqial
2161  ddakinfnek  lsqlqtymiq  fdqyikdsyd  lhdlkiaian  iideiieklk  sldehyhirv
2221  nlvktihdlh  lfienidfnk  sgsstaswiq  nvdtkyqiri  qigeklqqlk  rhiqnidiqh
2281  lagklkqhie  aidvrvlldq  lgttisferi  ndvlehvkhf  vinligdfev  aekinafrak
2341  vhelieryev  dqqiqvlmdk  lvelahqykl  ketiqklsnv  lqqvkikdyf  eklvgfidda
2401  vkklnelsfk  tfiedvnkfl  dmlikklksf  dyhqfvdetn  dkirevtqrl  ngeiqalelp
2461  qkaealklfl  eetkatvavy  leslqdtkit  liinwlqeal  ssaslahmka  kfretledtr
```

FIG. 17B 2521 drmyqmdiqq elqrylslvg qvystlvtyi sdwwtlaakn ltdfaeqysi qdwakrmkal
2581 veqgftvpei ktilgtmpaf evslqalqka tfqtpdfivp ltdlripsvq infkdlknik
2641 ipsrfstpef tilntfhips ftidfvemkv kiirtidqml nselqwpvpd iylrdlkved
2701 iplaritlpd frlpeiaipe fiiptlnlnd fqvpdlhipe fqlphishti evptfgklys
2761 ilkiqsplft ldanadigng ttsaneagia asitakgesk levlnfdfqa naqlsnpkin
2821 plalkesvkf sskylrtehg semlffgnai egksntvasl htekntlels ngvivkinnq
2881 ltldsntkyf hklnipkldf ssqadlrnei ktllkaghia wtssgkgswk wacprfsdeg
2941 thesqisfti egpltsfgls nkinskhlrv nqnlvyesgs lnfskleiqs qvdsqhvghs
3001 vltakgmalf gegkaeftgr hdahlngkvi gtlknslffs aqpfeitast nnegnlkvrf
3061 plrltgkidf lnnyalflsp saqqaswqvs arfnqykynq nfsagnneni meahvginge
3121 anldflnipl tipemrlpyt iittpplkdf slwektglke flkttkqsfd lsvkaqykkn
3181 khrhsitnpl avlcefisqs iksfdrhfek nrnnaldfvt ksynetkikf dkykaekshd
3241 elprtfqipg ytvpvvnvev spftiemsaf gyvfpkavsm psfsilgsdv rvpsytlilp
3301 slelpvlhvp rnlklslpdf kelctishif ipamgnityd fsfkssvitl ntnaelfnqs
3361 divahllsss ssvidalqyk legttrltrk rglklatals lsnkfvegsh nstvslttkn
3421 mevsvatttk aqipilrmnf kqelngntks kptvsssmef kydfnssmly stakgavdhk
3481 lslesltsyf siesstkgdv kgsvlsreys gtiaseanty lnskstrssv klqgtskidd
3541 iwnlevkenf ageatlqriy slwehstknh lqleglfftn gehtskatle lspwqmsalv
3601 qvhasqpssf hdfpdlgqev alnantknqk irwknevrih sgsfqsqvel sndqekahld
3661 iagsleghlr flkniilpvy dkslwdflkl dvttsigrrq hlrvstafvy tknpngysfs
3721 ipvkvladkf iipglklndl nsvlvmptfh vpftdlqvps ckldfreiqi ykklrtssfa
3781 lnlptlpevk fpevdvltky sqpedslipf feitvpesql tvsqftlpks vsdgiaaldl
3841 navankiadf elptiivpeq tieipsikfs vpagivipsf qaltarfevd spvynatwsa

FIG. 17C

```
3901 slknkadyve tvldstcsst vqfleyelnv lgthkiedgt lasktkgtfa hrdfsaeyee
3961 dgkyeglqew egkahlniks paftdlhlry qkdkkgists aaspavgtvg mdmdedddfs
4021 kwnfyyspqs spdkkltifk telrvresde etqikvnwee eaasglltsl kdnvpkatgv
4081 lydyvnkyhw ehtgltlrev ssklrrnlqn naewvyqgai rqiddidvrf qkaasgttgt
4141 yqewkdkaqn lyqelltqeg qasfqglkdn vfdglvrvtq efhmkvkhli dslidflnfp
4201 rfqfpgkpgi ytreelctmf irevgtvlsq vyskvhngse ilfsyfqdlv itlpfelrkh
4261 klidvismyr ellkdlskea qevfkaiqsl kttevlrnlq dllqfifqli ednikqlkem
4321 kftylinyiq deintifsdy ipyvfkllke nlclnlhkfn efiqnelqea sqelqqihqy
4381 imalreeyfd psivgwtvky yeleekivsl iknllvalkd fhseyivsas nftsqlssqv
4441 eqflhrniqe ylsiltdpdg kgkekiaels ataqeiiksq aiatkkiisd yhqqfryklq
4501 dfsdqlsdyy ekfiaeskrl idlsiqnyht fliyitellk klqsttvmnp ymklapgelt
4561 iil (SEQ ID NO:1)
```

FIG. 17D

***Homo sapiens* cytokeratin 8**
GenBank AAA35763

```
  1  msirvtqksy kvstsgpraf ssrsytsgpg srissssfsr vgssnfrggl gggyggasgm
 61  ggitavtvnq sllsplvlev dpniqavrtq ekeqiktlnn kfasfidkvr fleqqnkmle
121  tkwsllqqqk tarsnmdnmf esyinnlrrq letlgqeklk leaelgnmqg lvedfknkye
181  deinkrteme nefvlikkdv deaymnkvel esrlegltde inflrqlyee eirelqsqis
241  dtsvvlsmdn srsldmdsii aevkaqyedi anrsraeaes myqikyeelq slagkhgddl
301  rrtkteisem nrnisrlqae ieglkgqras leaaiadaeq rgelaikdan aklseleaal
361  qrakqdmarq lreyqelmnv klaldieiat yrkllegees rlesgmqnms ihtkttggya
421  gglssayggs qaglsyslgs sfgsgagsss fsrtsssrav vvkkietrdg klvsessdvl
481  pk (SEQ ID NO:2)
```

FIG. 18

SEQUENCE LISTING

<160> NUMBER OF SEQ ID NOS: 2

<210> SEQ ID NO 1
<211> LENGTH: 4563
<212> TYPE: PRT

<213> ORGANISM: Homo sapiens

<400> SEQUENCE: 1

```
Met Asp Pro Pro Arg Pro Ala Leu Leu Ala Leu Leu Ala Leu Pro Ala
1               5                   10                  15
Leu Leu Leu Leu Leu Leu Ala Gly Ala Arg Ala Glu Glu Glu Met Leu
            20                  25                  30
Glu Asn Val Ser Leu Val Cys Pro Lys Asp Ala Thr Arg Phe Lys His
        35                  40                  45
Leu Arg Lys Tyr Thr Tyr Asn Tyr Glu Ala Glu Ser Ser Ser Gly Val
    50                  55                  60
Pro Gly Thr Ala Asp Ser Arg Ser Ala Thr Arg Ile Asn Cys Lys Val
65                  70                  75                  80
Glu Leu Glu Val Pro Gln Leu Cys Ser Phe Ile Leu Lys Thr Ser Gln
                85                  90                  95
Cys Thr Leu Lys Glu Val Tyr Gly Phe Asn Pro Glu Gly Lys Ala Leu
            100                 105                 110
Leu Lys Lys Thr Lys Asn Ser Glu Glu Phe Ala Ala Ala Met Ser Arg
        115                 120                 125
Tyr Glu Leu Lys Leu Ala Ile Pro Glu Gly Lys Gln Val Phe Leu Tyr
    130                 135                 140
Pro Glu Lys Asp Glu Pro Thr Tyr Ile Leu Asn Ile Lys Arg Gly Ile
145                 150                 155                 160
Ile Ser Ala Leu Leu Val Pro Pro Glu Thr Glu Glu Ala Lys Gln Val
                165                 170                 175
Leu Phe Leu Asp Thr Val Tyr Gly Asn Cys Ser Thr His Phe Thr Val
            180                 185                 190
Lys Thr Arg Lys Gly Asn Val Ala Thr Glu Ile Ser Thr Glu Arg Asp
        195                 200                 205
Leu Gly Gln Cys Asp Arg Phe Lys Pro Ile Arg Thr Gly Ile Ser Pro
    210                 215                 220
Leu Ala Leu Ile Lys Gly Met Thr Arg Pro Leu Ser Thr Leu Ile Ser
225                 230                 235                 240
Ser Ser Gln Ser Cys Gln Tyr Thr Leu Asp Ala Lys Arg Lys His Val
                245                 250                 255
Ala Glu Ala Ile Cys Lys Glu Gln His Leu Phe Leu Pro Phe Ser Tyr
            260                 265                 270
Lys Asn Lys Tyr Gly Met Val Ala Gln Val Thr Gln Thr Leu Lys Leu
        275                 280                 285
Glu Asp Thr Pro Lys Ile Asn Ser Arg Phe Phe Gly Glu Gly Thr Lys
    290                 295                 300
Lys Met Gly Leu Ala Phe Glu Ser Thr Lys Ser Thr Ser Pro Pro Lys
305                 310                 315                 320
Gln Ala Glu Ala Val Leu Lys Thr Leu Gln Glu Leu Lys Lys Leu Thr
                325                 330                 335
Ile Ser Glu Gln Asn Ile Gln Arg Ala Asn Leu Phe Asn Lys Leu Val
            340                 345                 350
Thr Glu Leu Arg Gly Leu Ser Asp Glu Ala Val Thr Ser Leu Leu Pro
        355                 360                 365
Gln Leu Ile Glu Val Ser Ser Pro Ile Thr Leu Gln Ala Leu Val Gln
    370                 375                 380
Cys Gly Gln Pro Gln Cys Ser Thr His Ile Leu Gln Trp Leu Lys Arg
385                 390                 395                 400
```

```
Val His Ala Asn Pro Leu Leu Ile Asp Val Val Thr Tyr Leu Val Ala
                405                 410                 415
Leu Ile Pro Glu Pro Ser Ala Gln Gln Leu Arg Glu Ile Phe Asn Met
            420                 425                 430
Ala Arg Asp Gln Arg Ser Arg Ala Thr Leu Tyr Ala Leu Ser His Ala
        435                 440                 445
Val Asn Asn Tyr His Lys Thr Asn Pro Thr Gly Thr Gln Glu Leu Leu
    450                 455                 460
Asp Ile Ala Asn Tyr Leu Met Glu Gln Ile Gln Asp Asp Cys Thr Gly
465                 470                 475                 480
Asp Glu Asp Tyr Thr Tyr Leu Ile Leu Arg Val Ile Gly Asn Met Gly
                485                 490                 495
Gln Thr Met Glu Gln Leu Thr Pro Glu Leu Lys Ser Ser Ile Leu Lys
            500                 505                 510
Cys Val Gln Ser Thr Lys Pro Ser Leu Met Ile Gln Lys Ala Ala Ile
        515                 520                 525
Gln Ala Leu Arg Lys Met Glu Pro Lys Asp Lys Asp Gln Glu Val Leu
    530                 535                 540
Leu Gln Thr Phe Leu Asp Asp Ala Ser Pro Gly Asp Lys Arg Leu Ala
545                 550                 555                 560
Ala Tyr Leu Met Leu Met Arg Ser Pro Ser Gln Ala Asp Ile Asn Lys
                565                 570                 575
Ile Val Gln Ile Leu Pro Trp Glu Gln Asn Glu Gln Val Lys Asn Phe
            580                 585                 590
Val Ala Ser His Ile Ala Asn Ile Leu Asn Ser Glu Glu Leu Asp Ile
        595                 600                 605
Gln Asp Leu Lys Lys Leu Val Lys Glu Ala Leu Lys Glu Ser Gln Leu
    610                 615                 620
Pro Thr Val Met Asp Phe Arg Lys Phe Ser Arg Asn Tyr Gln Leu Tyr
625                 630                 635                 640
Lys Ser Val Ser Leu Pro Ser Leu Asp Pro Ala Ser Ala Lys Ile Glu
                645                 650                 655
Gly Asn Leu Ile Phe Asp Pro Asn Asn Tyr Leu Pro Lys Glu Ser Met
            660                 665                 670
Leu Lys Thr Thr Leu Thr Ala Phe Gly Phe Ala Ser Ala Asp Leu Ile
        675                 680                 685
Glu Ile Gly Leu Glu Gly Lys Gly Phe Glu Pro Thr Leu Glu Ala Leu
    690                 695                 700
Phe Gly Lys Gln Gly Phe Phe Pro Asp Ser Val Asn Lys Ala Leu Tyr
705                 710                 715                 720
Trp Val Asn Gly Gln Val Pro Asp Gly Val Ser Lys Val Leu Val Asp
                725                 730                 735
His Phe Gly Tyr Thr Lys Asp Asp Lys His Glu Gln Asp Met Val Asn
            740                 745                 750
Gly Ile Met Leu Ser Val Glu Lys Leu Ile Lys Asp Leu Lys Ser Lys
        755                 760                 765
Glu Val Pro Glu Ala Arg Ala Tyr Leu Arg Ile Leu Gly Glu Glu Leu
    770                 775                 780
Gly Phe Ala Ser Leu His Asp Leu Gln Leu Leu Gly Lys Leu Leu Leu
785                 790                 795                 800
Met Gly Ala Arg Thr Leu Gln Gly Ile Pro Gln Met Ile Gly Glu Val
                805                 810                 815
Ile Arg Lys Gly Ser Lys Asn Asp Phe Phe Leu His Tyr Ile Phe Met
```

-continued

```
               820                 825                 830
Glu Asn Ala Phe Glu Leu Pro Thr Gly Ala Gly Leu Gln Leu Gln Ile
            835                 840                 845
Ser Ser Ser Gly Val Ile Ala Pro Gly Ala Lys Ala Gly Val Lys Leu
850                 855                 860
Glu Val Ala Asn Met Gln Ala Glu Leu Val Ala Lys Pro Ser Val Ser
865                 870                 875                 880
Val Glu Phe Val Thr Asn Met Gly Ile Ile Pro Asp Phe Ala Arg
                885                 890                 895
Ser Gly Val Gln Met Asn Thr Asn Phe Phe His Glu Ser Gly Leu Glu
            900                 905                 910
Ala His Val Ala Leu Lys Ala Gly Lys Leu Lys Phe Ile Ile Pro Ser
            915                 920                 925
Pro Lys Arg Pro Val Lys Leu Leu Ser Gly Gly Asn Thr Leu His Leu
            930                 935                 940
Val Ser Thr Thr Lys Thr Glu Val Ile Pro Pro Leu Ile Glu Asn Arg
945                 950                 955                 960
Gln Ser Trp Ser Val Cys Lys Gln Val Phe Pro Gly Leu Asn Tyr Cys
                965                 970                 975
Thr Ser Gly Ala Tyr Ser Asn Ala Ser Ser Thr Asp Ser Ala Ser Tyr
            980                 985                 990
Tyr Pro Leu Thr Gly Asp Thr Arg Leu Glu Leu Glu Leu Arg Pro Thr
            995                 1000                1005
Gly Glu Ile Glu Gln Tyr Ser Val Ser Ala Thr Tyr Glu Leu Gln
    1010                1015                1020
Arg Glu Asp Arg Ala Leu Val Asp Thr Leu Lys Phe Val Thr Gln
    1025                1030                1035
Ala Glu Gly Ala Lys Gln Thr Glu Ala Thr Met Thr Phe Lys Tyr
    1040                1045                1050
Asn Arg Gln Ser Met Thr Leu Ser Ser Glu Val Gln Ile Pro Asp
    1055                1060                1065
Phe Asp Val Asp Leu Gly Thr Ile Leu Arg Val Asn Asp Glu Ser
    1070                1075                1080
Thr Glu Gly Lys Thr Ser Tyr Arg Leu Thr Leu Asp Ile Gln Asn
    1085                1090                1095
Lys Lys Ile Thr Glu Val Ala Leu Met Gly His Leu Ser Cys Asp
    1100                1105                1110
Thr Lys Glu Glu Arg Lys Ile Lys Gly Val Ile Ser Ile Pro Arg
    1115                1120                1125
Leu Gln Ala Glu Ala Arg Ser Glu Ile Leu Ala His Trp Ser Pro
    1130                1135                1140
Ala Lys Leu Leu Leu Gln Met Asp Ser Ser Ala Thr Ala Tyr Gly
    1145                1150                1155
Ser Thr Val Ser Lys Arg Val Ala Trp His Tyr Asp Glu Glu Lys
    1160                1165                1170
Ile Glu Phe Glu Trp Asn Thr Gly Thr Asn Val Asp Thr Lys Lys
    1175                1180                1185
Met Thr Ser Asn Phe Pro Val Asp Leu Ser Asp Tyr Pro Lys Ser
    1190                1195                1200
Leu His Met Tyr Ala Asn Arg Leu Leu Asp His Arg Val Pro Gln
    1205                1210                1215
Thr Asp Met Thr Phe Arg His Val Gly Ser Lys Leu Ile Val Ala
    1220                1225                1230
```

```
Met Ser Ser Trp Leu Gln Lys Ala Ser Gly Ser Leu Pro Tyr Thr
    1235            1240                1245

Gln Thr Leu Gln Asp His Leu Asn Ser Leu Lys Glu Phe Asn Leu
    1250            1255                1260

Gln Asn Met Gly Leu Pro Asp Phe His Ile Pro Glu Asn Leu Phe
    1265            1270                1275

Leu Lys Ser Asp Gly Arg Val Lys Tyr Thr Leu Asn Lys Asn Ser
    1280            1285                1290

Leu Lys Ile Glu Ile Pro Leu Pro Phe Gly Gly Lys Ser Ser Arg
    1295            1300                1305

Asp Leu Lys Met Leu Glu Thr Val Arg Thr Pro Ala Leu His Phe
    1310            1315                1320

Lys Ser Val Gly Phe His Leu Pro Ser Arg Glu Phe Gln Val Pro
    1325            1330                1335

Thr Phe Thr Ile Pro Lys Leu Tyr Gln Leu Gln Val Pro Leu Leu
    1340            1345                1350

Gly Val Leu Asp Leu Ser Thr Asn Val Tyr Ser Asn Leu Tyr Asn
    1355            1360                1365

Trp Ser Ala Ser Tyr Ser Gly Gly Asn Thr Ser Thr Asp His Phe
    1370            1375                1380

Ser Leu Arg Ala Arg Tyr His Met Lys Ala Asp Ser Val Val Asp
    1385            1390                1395

Leu Leu Ser Tyr Asn Val Gln Gly Ser Gly Glu Thr Thr Tyr Asp
    1400            1405                1410

His Lys Asn Thr Phe Thr Leu Ser Cys Asp Gly Ser Leu Arg His
    1415            1420                1425

Lys Phe Leu Asp Ser Asn Ile Lys Phe Ser His Val Glu Lys Leu
    1430            1435                1440

Gly Asn Asn Pro Val Ser Lys Gly Leu Leu Ile Phe Asp Ala Ser
    1445            1450                1455

Ser Ser Trp Gly Pro Gln Met Ser Ala Ser Val His Leu Asp Ser
    1460            1465                1470

Lys Lys Lys Gln His Leu Phe Val Lys Glu Val Lys Ile Asp Gly
    1475            1480                1485

Gln Phe Arg Val Ser Ser Phe Tyr Ala Lys Gly Thr Tyr Gly Leu
    1490            1495                1500

Ser Cys Gln Arg Asp Pro Asn Thr Gly Arg Leu Asn Gly Glu Ser
    1505            1510                1515

Asn Leu Arg Phe Asn Ser Ser Tyr Leu Gln Gly Thr Asn Gln Ile
    1520            1525                1530

Thr Gly Arg Tyr Glu Asp Gly Thr Leu Ser Leu Thr Ser Thr Ser
    1535            1540                1545

Asp Leu Gln Ser Gly Ile Ile Lys Asn Thr Ala Ser Leu Lys Tyr
    1550            1555                1560

Glu Asn Tyr Glu Leu Thr Leu Lys Ser Asp Thr Asn Gly Lys Tyr
    1565            1570                1575

Lys Asn Phe Ala Thr Ser Asn Lys Met Asp Met Thr Phe Ser Lys
    1580            1585                1590

Gln Asn Ala Leu Leu Arg Ser Glu Tyr Gln Ala Asp Tyr Glu Ser
    1595            1600                1605

Leu Arg Phe Phe Ser Leu Leu Ser Gly Ser Leu Asn Ser His Gly
    1610            1615                1620
```

```
Leu Glu Leu Asn Ala Asp Ile Leu Gly Thr Asp Lys Ile Asn Ser
    1625            1630            1635

Gly Ala His Lys Ala Thr Leu Arg Ile Gly Gln Asp Gly Ile Ser
    1640            1645            1650

Thr Ser Ala Thr Thr Asn Leu Lys Cys Ser Leu Leu Val Leu Glu
    1655            1660            1665

Asn Glu Leu Asn Ala Glu Leu Gly Leu Ser Gly Ala Ser Met Lys
    1670            1675            1680

Leu Thr Thr Asn Gly Arg Phe Arg Glu His Asn Ala Lys Phe Ser
    1685            1690            1695

Leu Asp Gly Lys Ala Ala Leu Thr Glu Leu Ser Leu Gly Ser Ala
    1700            1705            1710

Tyr Gln Ala Met Ile Leu Gly Val Asp Ser Lys Asn Ile Phe Asn
    1715            1720            1725

Phe Lys Val Ser Gln Glu Gly Leu Lys Leu Ser Asn Asp Met Met
    1730            1735            1740

Gly Ser Tyr Ala Glu Met Lys Phe Asp His Thr Asn Ser Leu Asn
    1745            1750            1755

Ile Ala Gly Leu Ser Leu Asp Phe Ser Ser Lys Leu Asp Asn Ile
    1760            1765            1770

Tyr Ser Ser Asp Lys Phe Tyr Lys Gln Thr Val Asn Leu Gln Leu
    1775            1780            1785

Gln Pro Tyr Ser Leu Val Thr Thr Leu Asn Ser Asp Leu Lys Tyr
    1790            1795            1800

Asn Ala Leu Asp Leu Thr Asn Asn Gly Lys Leu Arg Leu Glu Pro
    1805            1810            1815

Leu Lys Leu His Val Ala Gly Asn Leu Lys Gly Ala Tyr Gln Asn
    1820            1825            1830

Asn Glu Ile Lys His Ile Tyr Ala Ile Ser Ser Ala Ala Leu Ser
    1835            1840            1845

Ala Ser Tyr Lys Ala Asp Thr Val Ala Lys Val Gln Gly Val Glu
    1850            1855            1860

Phe Ser His Arg Leu Asn Thr Asp Ile Ala Gly Leu Ala Ser Ala
    1865            1870            1875

Ile Asp Met Ser Thr Asn Tyr Asn Ser Asp Ser Leu His Phe Ser
    1880            1885            1890

Asn Val Phe Arg Ser Val Met Ala Pro Phe Thr Met Thr Ile Asp
    1895            1900            1905

Ala His Thr Asn Gly Asn Gly Lys Leu Ala Leu Trp Gly Glu His
    1910            1915            1920

Thr Gly Gln Leu Tyr Ser Lys Phe Leu Leu Lys Ala Glu Pro Leu
    1925            1930            1935

Ala Phe Thr Phe Ser His Asp Tyr Lys Gly Ser Thr Ser His His
    1940            1945            1950

Leu Val Ser Arg Lys Ser Ile Ser Ala Ala Leu Glu His Lys Val
    1955            1960            1965

Ser Ala Leu Leu Thr Pro Ala Glu Gln Thr Gly Thr Trp Lys Leu
    1970            1975            1980

Lys Thr Gln Phe Asn Asn Asn Glu Tyr Ser Gln Asp Leu Asp Ala
    1985            1990            1995

Tyr Asn Thr Lys Asp Lys Ile Gly Val Glu Leu Thr Gly Arg Thr
    2000            2005            2010

Leu Ala Asp Leu Thr Leu Leu Asp Ser Pro Ile Lys Val Pro Leu
```

-continued

```
              2015                2020                2025
Leu Leu Ser Glu Pro Ile Asn Ile Ile Asp Ala Leu Glu Met Arg
         2030                2035                2040

Asp Ala Val Glu Lys Pro Gln Glu Phe Thr Ile Val Ala Phe Val
         2045                2050                2055

Lys Tyr Asp Lys Asn Gln Asp Val His Ser Ile Asn Leu Pro Phe
         2060                2065                2070

Phe Glu Thr Leu Gln Glu Tyr Phe Glu Arg Asn Arg Gln Thr Ile
         2075                2080                2085

Ile Val Val Leu Glu Asn Val Gln Arg Asn Leu Lys His Ile Asn
         2090                2095                2100

Ile Asp Gln Phe Val Arg Lys Tyr Arg Ala Ala Leu Gly Lys Leu
         2105                2110                2115

Pro Gln Gln Ala Asn Asp Tyr Leu Asn Ser Phe Asn Trp Glu Arg
         2120                2125                2130

Gln Val Ser His Ala Lys Glu Lys Leu Thr Ala Leu Thr Lys Lys
         2135                2140                2145

Tyr Arg Ile Thr Glu Asn Asp Ile Gln Ile Ala Leu Asp Asp Ala
         2150                2155                2160

Lys Ile Asn Phe Asn Glu Lys Leu Ser Gln Leu Gln Thr Tyr Met
         2165                2170                2175

Ile Gln Phe Asp Gln Tyr Ile Lys Asp Ser Tyr Asp Leu His Asp
         2180                2185                2190

Leu Lys Ile Ala Ile Ala Asn Ile Ile Asp Glu Ile Ile Glu Lys
         2195                2200                2205

Leu Lys Ser Leu Asp Glu His Tyr His Ile Arg Val Asn Leu Val
         2210                2215                2220

Lys Thr Ile His Asp Leu His Leu Phe Ile Glu Asn Ile Asp Phe
         2225                2230                2235

Asn Lys Ser Gly Ser Ser Thr Ala Ser Trp Ile Gln Asn Val Asp
         2240                2245                2250

Thr Lys Tyr Gln Ile Arg Ile Gln Ile Gln Glu Lys Leu Gln Gln
         2255                2260                2265

Leu Lys Arg His Ile Gln Asn Ile Asp Ile Gln His Leu Ala Gly
         2270                2275                2280

Lys Leu Lys Gln His Ile Glu Ala Ile Asp Val Arg Val Leu Leu
         2285                2290                2295

Asp Gln Leu Gly Thr Thr Ile Ser Phe Glu Arg Ile Asn Asp Val
         2300                2305                2310

Leu Glu His Val Lys His Phe Val Ile Asn Leu Ile Gly Asp Phe
         2315                2320                2325

Glu Val Ala Glu Lys Ile Asn Ala Phe Arg Ala Lys Val His Glu
         2330                2335                2340

Leu Ile Glu Arg Tyr Glu Val Asp Gln Gln Ile Gln Val Leu Met
         2345                2350                2355

Asp Lys Leu Val Glu Leu Ala His Gln Tyr Lys Leu Lys Glu Thr
         2360                2365                2370

Ile Gln Lys Leu Ser Asn Val Leu Gln Gln Val Lys Ile Lys Asp
         2375                2380                2385

Tyr Phe Glu Lys Leu Val Gly Phe Ile Asp Asp Ala Val Lys Lys
         2390                2395                2400

Leu Asn Glu Leu Ser Phe Lys Thr Phe Ile Glu Asp Val Asn Lys
         2405                2410                2415
```

-continued

Phe Leu Asp Met Leu Ile Lys Lys Leu Lys Ser Phe Asp Tyr His
2420            2425                2430

Gln Phe Val Asp Glu Thr Asn Asp Lys Ile Arg Glu Val Thr Gln
2435            2440                2445

Arg Leu Asn Gly Glu Ile Gln Ala Leu Glu Leu Pro Gln Lys Ala
2450            2455                2460

Glu Ala Leu Lys Leu Phe Leu Glu Glu Thr Lys Ala Thr Val Ala
2465            2470                2475

Val Tyr Leu Glu Ser Leu Gln Asp Thr Lys Ile Thr Leu Ile Ile
2480            2485                2490

Asn Trp Leu Gln Glu Ala Leu Ser Ser Ala Ser Leu Ala His Met
2495            2500                2505

Lys Ala Lys Phe Arg Glu Thr Leu Glu Asp Thr Arg Asp Arg Met
2510            2515                2520

Tyr Gln Met Asp Ile Gln Gln Glu Leu Gln Arg Tyr Leu Ser Leu
2525            2530                2535

Val Gly Gln Val Tyr Ser Thr Leu Val Thr Tyr Ile Ser Asp Trp
2540            2545                2550

Trp Thr Leu Ala Ala Lys Asn Leu Thr Asp Phe Ala Glu Gln Tyr
2555            2560                2565

Ser Ile Gln Asp Trp Ala Lys Arg Met Lys Ala Leu Val Glu Gln
2570            2575                2580

Gly Phe Thr Val Pro Glu Ile Lys Thr Ile Leu Gly Thr Met Pro
2585            2590                2595

Ala Phe Glu Val Ser Leu Gln Ala Leu Gln Lys Ala Thr Phe Gln
2600            2605                2610

Thr Pro Asp Phe Ile Val Pro Leu Thr Asp Leu Arg Ile Pro Ser
2615            2620                2625

Val Gln Ile Asn Phe Lys Asp Leu Lys Asn Ile Lys Ile Pro Ser
2630            2635                2640

Arg Phe Ser Thr Pro Glu Phe Thr Ile Leu Asn Thr Phe His Ile
2645            2650                2655

Pro Ser Phe Thr Ile Asp Phe Val Glu Met Lys Val Lys Ile Ile
2660            2665                2670

Arg Thr Ile Asp Gln Met Leu Asn Ser Glu Leu Gln Trp Pro Val
2675            2680                2685

Pro Asp Ile Tyr Leu Arg Asp Leu Lys Val Glu Asp Ile Pro Leu
2690            2695                2700

Ala Arg Ile Thr Leu Pro Asp Phe Arg Leu Pro Glu Ile Ala Ile
2705            2710                2715

Pro Glu Phe Ile Ile Pro Thr Leu Asn Leu Asn Asp Phe Gln Val
2720            2725                2730

Pro Asp Leu His Ile Pro Glu Phe Gln Leu Pro His Ile Ser His
2735            2740                2745

Thr Ile Glu Val Pro Thr Phe Gly Lys Leu Tyr Ser Ile Leu Lys
2750            2755                2760

Ile Gln Ser Pro Leu Phe Thr Leu Asp Ala Asn Ala Asp Ile Gly
2765            2770                2775

Asn Gly Thr Thr Ser Ala Asn Glu Ala Gly Ile Ala Ala Ser Ile
2780            2785                2790

Thr Ala Lys Gly Glu Ser Lys Leu Glu Val Leu Asn Phe Asp Phe
2795            2800                2805

```
Gln Ala Asn Ala Gln Leu Ser Asn Pro Lys Ile Asn Pro Leu Ala
2810                2815                2820

Leu Lys Glu Ser Val Lys Phe Ser Ser Lys Tyr Leu Arg Thr Glu
2825                2830                2835

His Gly Ser Glu Met Leu Phe Phe Gly Asn Ala Ile Glu Gly Lys
2840                2845                2850

Ser Asn Thr Val Ala Ser Leu His Thr Glu Lys Asn Thr Leu Glu
2855                2860                2865

Leu Ser Asn Gly Val Ile Val Lys Ile Asn Asn Gln Leu Thr Leu
2870                2875                2880

Asp Ser Asn Thr Lys Tyr Phe His Lys Leu Asn Ile Pro Lys Leu
2885                2890                2895

Asp Phe Ser Ser Gln Ala Asp Leu Arg Asn Glu Ile Lys Thr Leu
2900                2905                2910

Leu Lys Ala Gly His Ile Ala Trp Thr Ser Ser Gly Lys Gly Ser
2915                2920                2925

Trp Lys Trp Ala Cys Pro Arg Phe Ser Asp Glu Gly Thr His Glu
2930                2935                2940

Ser Gln Ile Ser Phe Thr Ile Glu Gly Pro Leu Thr Ser Phe Gly
2945                2950                2955

Leu Ser Asn Lys Ile Asn Ser Lys His Leu Arg Val Asn Gln Asn
2960                2965                2970

Leu Val Tyr Glu Ser Gly Ser Leu Asn Phe Ser Lys Leu Glu Ile
2975                2980                2985

Gln Ser Gln Val Asp Ser Gln His Val Gly His Ser Val Leu Thr
2990                2995                3000

Ala Lys Gly Met Ala Leu Phe Gly Glu Gly Lys Ala Glu Phe Thr
3005                3010                3015

Gly Arg His Asp Ala His Leu Asn Gly Lys Val Ile Gly Thr Leu
3020                3025                3030

Lys Asn Ser Leu Phe Phe Ser Ala Gln Pro Phe Glu Ile Thr Ala
3035                3040                3045

Ser Thr Asn Asn Glu Gly Asn Leu Lys Val Arg Phe Pro Leu Arg
3050                3055                3060

Leu Thr Gly Lys Ile Asp Phe Leu Asn Asn Tyr Ala Leu Phe Leu
3065                3070                3075

Ser Pro Ser Ala Gln Gln Ala Ser Trp Gln Val Ser Ala Arg Phe
3080                3085                3090

Asn Gln Tyr Lys Tyr Asn Gln Asn Phe Ser Ala Gly Asn Asn Glu
3095                3100                3105

Asn Ile Met Glu Ala His Val Gly Ile Asn Gly Glu Ala Asn Leu
3110                3115                3120

Asp Phe Leu Asn Ile Pro Leu Thr Ile Pro Glu Met Arg Leu Pro
3125                3130                3135

Tyr Thr Ile Ile Thr Thr Pro Pro Leu Lys Asp Phe Ser Leu Trp
3140                3145                3150

Glu Lys Thr Gly Leu Lys Glu Phe Leu Lys Thr Thr Lys Gln Ser
3155                3160                3165

Phe Asp Leu Ser Val Lys Ala Gln Tyr Lys Lys Asn Lys His Arg
3170                3175                3180

His Ser Ile Thr Asn Pro Leu Ala Val Leu Cys Glu Phe Ile Ser
3185                3190                3195

Gln Ser Ile Lys Ser Phe Asp Arg His Phe Glu Lys Asn Arg Asn
```

```
                3200                3205                3210
Asn Ala Leu Asp Phe Val Thr Lys Ser Tyr Asn Glu Thr Lys Ile
    3215                3220                3225
Lys Phe Asp Lys Tyr Lys Ala Glu Lys Ser His Asp Glu Leu Pro
    3230                3235                3240
Arg Thr Phe Gln Ile Pro Gly Tyr Thr Val Pro Val Val Asn Val
    3245                3250                3255
Glu Val Ser Pro Phe Thr Ile Glu Met Ser Ala Phe Gly Tyr Val
    3260                3265                3270
Phe Pro Lys Ala Val Ser Met Pro Ser Phe Ser Ile Leu Gly Ser
    3275                3280                3285
Asp Val Arg Val Pro Ser Tyr Thr Leu Ile Leu Pro Ser Leu Glu
    3290                3295                3300
Leu Pro Val Leu His Val Pro Arg Asn Leu Lys Leu Ser Leu Pro
    3305                3310                3315
Asp Phe Lys Glu Leu Cys Thr Ile Ser His Ile Phe Ile Pro Ala
    3320                3325                3330
Met Gly Asn Ile Thr Tyr Asp Phe Ser Phe Lys Ser Ser Val Ile
    3335                3340                3345
Thr Leu Asn Thr Asn Ala Glu Leu Phe Asn Gln Ser Asp Ile Val
    3350                3355                3360
Ala His Leu Leu Ser Ser Ser Ser Val Ile Asp Ala Leu Gln
    3365                3370                3375
Tyr Lys Leu Glu Gly Thr Thr Arg Leu Thr Arg Lys Arg Gly Leu
    3380                3385                3390
Lys Leu Ala Thr Ala Leu Ser Leu Ser Asn Lys Phe Val Glu Gly
    3395                3400                3405
Ser His Asn Ser Thr Val Ser Leu Thr Thr Lys Asn Met Glu Val
    3410                3415                3420
Ser Val Ala Thr Thr Lys Ala Gln Ile Pro Ile Leu Arg Met
    3425                3430                3435
Asn Phe Lys Gln Glu Leu Asn Gly Asn Thr Lys Ser Lys Pro Thr
    3440                3445                3450
Val Ser Ser Ser Met Glu Phe Lys Tyr Asp Phe Asn Ser Ser Met
    3455                3460                3465
Leu Tyr Ser Thr Ala Lys Gly Ala Val Asp His Lys Leu Ser Leu
    3470                3475                3480
Glu Ser Leu Thr Ser Tyr Phe Ser Ile Glu Ser Ser Thr Lys Gly
    3485                3490                3495
Asp Val Lys Gly Ser Val Leu Ser Arg Glu Tyr Ser Gly Thr Ile
    3500                3505                3510
Ala Ser Glu Ala Asn Thr Tyr Leu Asn Ser Lys Ser Thr Arg Ser
    3515                3520                3525
Ser Val Lys Leu Gln Gly Thr Ser Lys Ile Asp Asp Ile Trp Asn
    3530                3535                3540
Leu Glu Val Lys Glu Asn Phe Ala Gly Glu Ala Thr Leu Gln Arg
    3545                3550                3555
Ile Tyr Ser Leu Trp Glu His Ser Thr Lys Asn His Leu Gln Leu
    3560                3565                3570
Glu Gly Leu Phe Phe Thr Asn Gly Glu His Thr Ser Lys Ala Thr
    3575                3580                3585
Leu Glu Leu Ser Pro Trp Gln Met Ser Ala Leu Val Gln Val His
    3590                3595                3600
```

-continued

```
Ala Ser Gln Pro Ser Ser Phe His Asp Phe Pro Asp Leu Gly Gln
3605                3610                3615

Glu Val Ala Leu Asn Ala Asn Thr Lys Asn Gln Lys Ile Arg Trp
3620                3625                3630

Lys Asn Glu Val Arg Ile His Ser Gly Ser Phe Gln Ser Gln Val
3635                3640                3645

Glu Leu Ser Asn Asp Gln Glu Lys Ala His Leu Asp Ile Ala Gly
3650                3655                3660

Ser Leu Glu Gly His Leu Arg Phe Leu Lys Asn Ile Ile Leu Pro
3665                3670                3675

Val Tyr Asp Lys Ser Leu Trp Asp Phe Leu Lys Leu Asp Val Thr
3680                3685                3690

Thr Ser Ile Gly Arg Arg Gln His Leu Arg Val Ser Thr Ala Phe
3695                3700                3705

Val Tyr Thr Lys Asn Pro Asn Gly Tyr Ser Phe Ser Ile Pro Val
3710                3715                3720

Lys Val Leu Ala Asp Lys Phe Ile Ile Pro Gly Leu Lys Leu Asn
3725                3730                3735

Asp Leu Asn Ser Val Leu Val Met Pro Thr Phe His Val Pro Phe
3740                3745                3750

Thr Asp Leu Gln Val Pro Ser Cys Lys Leu Asp Phe Arg Glu Ile
3755                3760                3765

Gln Ile Tyr Lys Lys Leu Arg Thr Ser Ser Phe Ala Leu Asn Leu
3770                3775                3780

Pro Thr Leu Pro Glu Val Lys Phe Pro Glu Val Asp Val Leu Thr
3785                3790                3795

Lys Tyr Ser Gln Pro Glu Asp Ser Leu Ile Pro Phe Phe Glu Ile
3800                3805                3810

Thr Val Pro Glu Ser Gln Leu Thr Val Ser Gln Phe Thr Leu Pro
3815                3820                3825

Lys Ser Val Ser Asp Gly Ile Ala Ala Leu Asp Leu Asn Ala Val
3830                3835                3840

Ala Asn Lys Ile Ala Asp Phe Glu Leu Pro Thr Ile Ile Val Pro
3845                3850                3855

Glu Gln Thr Ile Glu Ile Pro Ser Ile Lys Phe Ser Val Pro Ala
3860                3865                3870

Gly Ile Val Ile Pro Ser Phe Gln Ala Leu Thr Ala Arg Phe Glu
3875                3880                3885

Val Asp Ser Pro Val Tyr Asn Ala Thr Trp Ser Ala Ser Leu Lys
3890                3895                3900

Asn Lys Ala Asp Tyr Val Glu Thr Val Leu Asp Ser Thr Cys Ser
3905                3910                3915

Ser Thr Val Gln Phe Leu Glu Tyr Glu Leu Asn Val Leu Gly Thr
3920                3925                3930

His Lys Ile Glu Asp Gly Thr Leu Ala Ser Lys Thr Lys Gly Thr
3935                3940                3945

Phe Ala His Arg Asp Phe Ser Ala Glu Tyr Glu Glu Asp Gly Lys
3950                3955                3960

Tyr Glu Gly Leu Gln Glu Trp Glu Gly Lys Ala His Leu Asn Ile
3965                3970                3975

Lys Ser Pro Ala Phe Thr Asp Leu His Leu Arg Tyr Gln Lys Asp
3980                3985                3990
```

-continued

| | | | | | | | | | | | |
|---|---|---|---|---|---|---|---|---|---|---|---|
| Lys | Lys 3995 | Gly | Ile | Ser | Thr 4000 | Ser | Ala | Ala | Ser 4005 | Pro | Ala | Val | Gly | Thr |
| Val 4010 | Gly | Met | Asp | Met 4015 | Asp | Glu | Asp | Asp | Phe 4020 | Ser | Lys | Trp | Asn |
| Phe 4025 | Tyr | Tyr | Ser | Pro 4030 | Gln | Ser | Ser | Pro | Asp 4035 | Lys | Lys | Leu | Thr | Ile |
| Phe 4040 | Lys | Thr | Glu | Leu 4045 | Arg | Val | Arg | Glu | Ser 4050 | Asp | Glu | Glu | Thr | Gln |
| Ile 4055 | Lys | Val | Asn | Trp 4060 | Glu | Glu | Ala | Ala | Ser 4065 | Gly | Leu | Leu | Thr |
| Ser 4070 | Leu | Lys | Asp | Asn 4075 | Val | Pro | Lys | Ala | Thr 4080 | Gly | Val | Leu | Tyr | Asp |
| Tyr 4085 | Val | Asn | Lys | Tyr 4090 | His | Trp | Glu | His | Thr 4095 | Gly | Leu | Thr | Leu | Arg |
| Glu 4100 | Val | Ser | Ser | Lys 4105 | Leu | Arg | Arg | Asn | Leu 4110 | Gln | Asn | Asn | Ala | Glu |
| Trp 4115 | Val | Tyr | Gln | Gly 4120 | Ala | Ile | Arg | Gln | Ile 4125 | Asp | Asp | Ile | Asp | Val |
| Arg 4130 | Phe | Gln | Lys | Ala 4135 | Ala | Ser | Gly | Thr | Thr 4140 | Gly | Thr | Tyr | Gln | Glu |
| Trp 4145 | Lys | Asp | Lys | Ala 4150 | Gln | Asn | Leu | Tyr | Gln 4155 | Glu | Leu | Leu | Thr | Gln |
| Glu 4160 | Gly | Gln | Ala | Ser 4165 | Phe | Gln | Gly | Leu | Lys 4170 | Asp | Asn | Val | Phe | Asp |
| Gly 4175 | Leu | Val | Arg | Val 4180 | Thr | Gln | Glu | Phe | His 4185 | Met | Lys | Val | Lys | His |
| Leu 4190 | Ile | Asp | Ser | Leu 4195 | Ile | Asp | Phe | Leu | Asn 4200 | Phe | Pro | Arg | Phe | Gln |
| Phe 4205 | Pro | Gly | Lys | Pro 4210 | Gly | Ile | Tyr | Thr | Arg 4215 | Glu | Glu | Leu | Cys | Thr |
| Met 4220 | Phe | Ile | Arg | Glu 4225 | Val | Gly | Thr | Val | Leu 4230 | Ser | Gln | Val | Tyr | Ser |
| Lys 4235 | Val | His | Asn | Gly 4240 | Ser | Glu | Ile | Leu | Phe 4245 | Ser | Tyr | Phe | Gln | Asp |
| Leu 4250 | Val | Ile | Thr | Leu 4255 | Pro | Phe | Glu | Leu | Arg 4260 | Lys | His | Lys | Leu | Ile |
| Asp 4265 | Val | Ile | Ser | Met 4270 | Tyr | Arg | Glu | Leu | Leu 4275 | Lys | Asp | Leu | Ser | Lys |
| Glu 4280 | Ala | Gln | Glu | Val 4285 | Phe | Lys | Ala | Ile | Gln 4290 | Ser | Leu | Lys | Thr | Thr |
| Glu 4295 | Val | Leu | Arg | Asn 4300 | Leu | Gln | Asp | Leu | Leu 4305 | Gln | Phe | Ile | Phe | Gln |
| Leu 4310 | Ile | Glu | Asp | Asn 4315 | Ile | Lys | Gln | Leu | Lys 4320 | Glu | Met | Lys | Phe | Thr |
| Tyr 4325 | Leu | Ile | Asn | Tyr 4330 | Ile | Gln | Asp | Glu | Ile 4335 | Asn | Thr | Ile | Phe | Ser |
| Asp 4340 | Tyr | Ile | Pro | Tyr 4345 | Val | Phe | Lys | Leu | Leu 4350 | Lys | Glu | Asn | Leu | Cys |
| Leu 4355 | Asn | Leu | His | Lys 4360 | Phe | Asn | Glu | Phe | Ile 4365 | Gln | Asn | Glu | Leu | Gln |
| Glu 4370 | Ala | Ser | Gln | Glu 4375 | Leu | Gln | Gln | Ile | His 4380 | Gln | Tyr | Ile | Met | Ala |
| Leu | Arg | Glu | Glu | Tyr | Phe | Asp | Pro | Ser | Ile | Val | Gly | Trp | Thr | Val |

```
      4385                4390                4395
Lys  Tyr  Tyr  Glu  Leu  Glu  Glu  Lys  Ile  Val  Ser  Leu  Ile  Lys  Asn
      4400                4405                4410

Leu  Leu  Val  Ala  Leu  Lys  Asp  Phe  His  Ser  Glu  Tyr  Ile  Val  Ser
      4415                4420                4425

Ala  Ser  Asn  Phe  Thr  Ser  Gln  Leu  Ser  Ser  Gln  Val  Glu  Gln  Phe
      4430                4435                4440

Leu  His  Arg  Asn  Ile  Gln  Glu  Tyr  Leu  Ser  Ile  Leu  Thr  Asp  Pro
      4445                4450                4455

Asp  Gly  Lys  Gly  Lys  Glu  Lys  Ile  Ala  Glu  Leu  Ser  Ala  Thr  Ala
      4460                4465                4470

Gln  Glu  Ile  Ile  Lys  Ser  Gln  Ala  Ile  Ala  Thr  Lys  Lys  Ile  Ile
      4475                4480                4485

Ser  Asp  Tyr  His  Gln  Gln  Phe  Arg  Tyr  Lys  Leu  Gln  Asp  Phe  Ser
      4490                4495                4500

Asp  Gln  Leu  Ser  Asp  Tyr  Tyr  Glu  Lys  Phe  Ile  Ala  Glu  Ser  Lys
      4505                4510                4515

Arg  Leu  Ile  Asp  Leu  Ser  Ile  Gln  Asn  Tyr  His  Thr  Phe  Leu  Ile
      4520                4525                4530

Tyr  Ile  Thr  Glu  Leu  Leu  Lys  Lys  Leu  Gln  Ser  Thr  Thr  Val  Met
      4535                4540                4545

Asn  Pro  Tyr  Met  Lys  Leu  Ala  Pro  Gly  Glu  Leu  Thr  Ile  Ile  Leu
      4550                4555                4560

<210> SEQ ID NO 2
<211> LENGTH: 482
<212> TYPE: PRT
<213> ORGANISM: Homo sapiens

<400> SEQUENCE: 2

Met  Ser  Ile  Arg  Val  Thr  Gln  Lys  Ser  Tyr  Lys  Val  Ser  Thr  Ser  Gly
 1              5                  10                  15

Pro  Arg  Ala  Phe  Ser  Ser  Arg  Ser  Tyr  Thr  Ser  Gly  Pro  Gly  Ser  Arg
            20                  25                  30

Ile  Ser  Ser  Ser  Ser  Phe  Ser  Arg  Val  Gly  Ser  Ser  Asn  Phe  Arg  Gly
        35                  40                  45

Gly  Leu  Gly  Gly  Gly  Tyr  Gly  Gly  Ala  Ser  Gly  Met  Gly  Gly  Ile  Thr
    50                  55                  60

Ala  Val  Thr  Val  Asn  Gln  Ser  Leu  Leu  Ser  Pro  Leu  Val  Leu  Glu  Val
65                  70                  75                  80

Asp  Pro  Asn  Ile  Gln  Ala  Val  Arg  Thr  Gln  Glu  Lys  Glu  Gln  Ile  Lys
                85                  90                  95

Thr  Leu  Asn  Asn  Lys  Phe  Ala  Ser  Phe  Ile  Asp  Lys  Val  Arg  Phe  Leu
            100                 105                 110

Glu  Gln  Gln  Asn  Lys  Met  Leu  Glu  Thr  Lys  Trp  Ser  Leu  Leu  Gln  Gln
        115                 120                 125

Gln  Lys  Thr  Ala  Arg  Ser  Asn  Met  Asp  Asn  Met  Phe  Glu  Ser  Tyr  Ile
    130                 135                 140

Asn  Asn  Leu  Arg  Arg  Gln  Leu  Glu  Thr  Leu  Gly  Gln  Glu  Lys  Leu  Lys
145                 150                 155                 160

Leu  Glu  Ala  Glu  Leu  Gly  Asn  Met  Gln  Gly  Leu  Val  Glu  Asp  Phe  Lys
                165                 170                 175

Asn  Lys  Tyr  Glu  Asp  Glu  Ile  Asn  Lys  Arg  Thr  Glu  Met  Glu  Asn  Glu
            180                 185                 190
```

```
Phe Val Leu Ile Lys Lys Asp Val Asp Glu Ala Tyr Met Asn Lys Val
        195             200             205

Glu Leu Glu Ser Arg Leu Glu Gly Leu Thr Asp Glu Ile Asn Phe Leu
        210             215             220

Arg Gln Leu Tyr Glu Glu Ile Arg Glu Leu Gln Ser Gln Ile Ser
225             230             235             240

Asp Thr Ser Val Val Leu Ser Met Asp Asn Ser Arg Ser Leu Asp Met
            245             250             255

Asp Ser Ile Ile Ala Glu Val Lys Ala Gln Tyr Glu Asp Ile Ala Asn
            260             265             270

Arg Ser Arg Ala Glu Ala Glu Ser Met Tyr Gln Ile Lys Tyr Glu Glu
            275             280             285

Leu Gln Ser Leu Ala Gly Lys His Gly Asp Asp Leu Arg Arg Thr Lys
        290             295             300

Thr Glu Ile Ser Glu Met Asn Arg Asn Ile Ser Arg Leu Gln Ala Glu
305             310             315             320

Ile Glu Gly Leu Lys Gly Gln Arg Ala Ser Leu Glu Ala Ala Ile Ala
            325             330             335

Asp Ala Glu Gln Arg Gly Glu Leu Ala Ile Lys Asp Ala Asn Ala Lys
            340             345             350

Leu Ser Glu Leu Glu Ala Ala Leu Gln Arg Ala Lys Gln Asp Met Ala
        355             360             365

Arg Gln Leu Arg Glu Tyr Gln Glu Leu Met Asn Val Lys Leu Ala Leu
        370             375             380

Asp Ile Glu Ile Ala Thr Tyr Arg Lys Leu Leu Glu Gly Glu Glu Ser
385             390             395             400

Arg Leu Glu Ser Gly Met Gln Asn Met Ser Ile His Thr Lys Thr Thr
            405             410             415

Gly Gly Tyr Ala Gly Gly Leu Ser Ser Ala Tyr Gly Gly Ser Gln Ala
            420             425             430

Gly Leu Ser Tyr Ser Leu Gly Ser Ser Phe Gly Ser Gly Ala Gly Ser
        435             440             445

Ser Ser Phe Ser Arg Thr Ser Ser Ser Arg Ala Val Val Val Lys Lys
        450             455             460

Ile Glu Thr Arg Asp Gly Lys Leu Val Ser Glu Ser Ser Asp Val Leu
465             470             475             480

Pro Lys
```

ULTRA-SMALL APOB-CONTAINING PARTICLES AND METHODS OF USE THEREOF

CROSS-REFERENCE

This application is a continuation of U.S. patent application Ser. No. 14/123,927, filed Apr. 16, 2014, now U.S. Pat. No. 9,322,833, which is a national stage filing under 35 U.S.C. §371 of PCT/US2012/042513, filed Jun. 14, 2002, which claims the benefit of U.S. Provisional Patent Application No. 61/497,847, filed Jun. 16, 2011, each of which applications is incorporated herein by reference in its entirety.

BACKGROUND

Lipoproteins function to transport lipids around the body. Lipids are generally hydrophobic, while the extracellular environment is generally aqueous. Apolipoproteins bind to lipids, such as cholesterol and triglycerides, and facilitate their transport through the aqueous environment. Apolipoprotein B (apoB) represents most of the protein content in low density lipoprotein (LDL), and is also present in intermediate-density lipoproteins (IDL) and very low density lipoproteins (VLDL). Apolipoprotein AI (apoAI) is the principal protein in high density lipoprotein (HDL) and represents about 70%.

The total cholesterol/HDL cholesterol ratio and the LDL/HDL cholesterol ratio are two indicators of vascular disease risk, including cardiovascular disease (CVD) risk. For example, an increase in the total cholesterol concentration, and specifically LDL cholesterol, is an atherogenic lipid marker. Reduced HDL cholesterol concentration is associated with various risk factors, including components of the metabolic syndrome.

Literature

Millán et al. (2009) *Vascular Health and Risk Management* 5:757; Superko and Gadesam (2008) *Curr. Atheroscler. Rep.* 10:377; U.S. Pat. No. 7,781,219; U.S. Patent Publication No. 20100183607; U.S. Patent Publication No. 20100179066; U.S. Patent Publication No. 20090155915; WO 2010/115200; WO 2010/115094.

SUMMARY

The present disclosure describes a very high density, ultra small lipid depleted apolipoprotein B containing particle that may be indicative of increased cardiovascular disease risk. These particles may contain other proteins, such as cytokeratins. The isolated particles are useful in diagnostic assays, which are also provided.

BRIEF DESCRIPTION OF THE DRAWINGS

FIGS. 17A-D depicts an amino acid sequence of apoB-100.

FIG. 18 depicts an amino acid sequence of cytokeratin 8.

DEFINITIONS

Figure 1:
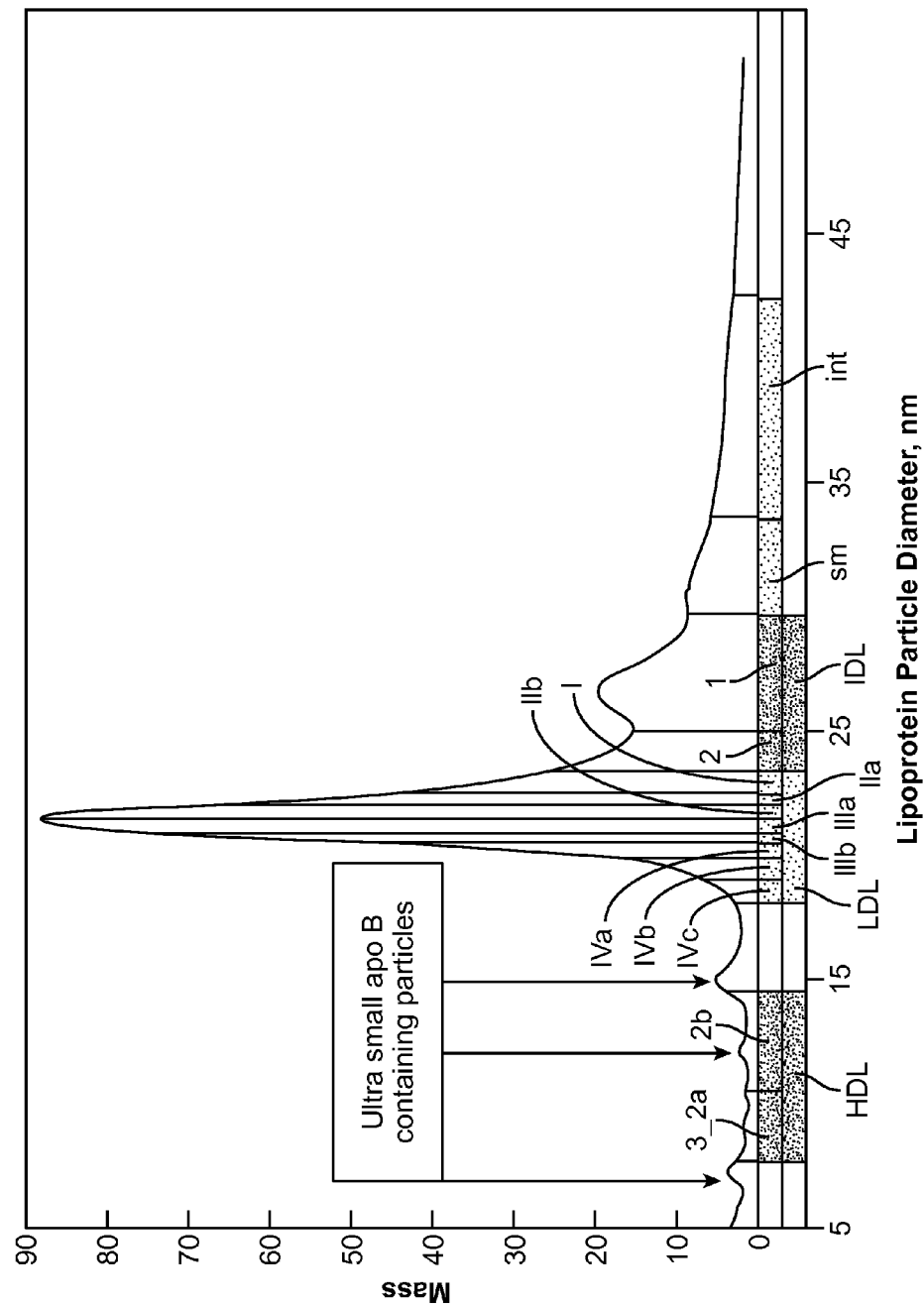
FIG. 1 depicts the ion mobility (IM) analysis of particles isolated from plasma from a representative individual using a specific anti-apoB antibody conjugated to magnetic beads.

As used herein, the terms "determining," "measuring," and "assessing," and "assaying" are used interchangeably and include both quantitative and qualitative determinations.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 80% free, at least 85% free, at least 90%, at least 95%, at least 98%, or at least 99%, free from other components with which it is naturally associated.

"Predisposition" as used herein is substantially synonymous with risk, inclination, tendency, predilection, or susceptibility.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some cases, the term refers to a human.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an apoB particle" includes a plurality of such particles and reference to "the diagnostic assay" includes reference to one or more diagnostic assays and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure describes a species of very high density, ultra small, lipid-depleted apolipoprotein B containing particles. These particles may contain other proteins including cytokeratins. The isolated particles are useful in diagnostic assays, which are also provided.

Apolipoprotein Particle

The present disclosure provides an isolated particle comprising: a) apolipoprotein B (apoB); and b) a cytokeratin-8 polypeptide having a molecular weight of about 52 kDa. A subject isolated particle is referred to herein as a "very high density, ultra small, de-lipidated apolipoprotein B containing particle". A subject "very high density, ultra small, de-lipidated apolipoprotein B containing particle" is characterized by having an average particle diameter in the range of from about 7.1 nm to about 22 nm; having a density greater than 1.21 g/mL; and having undetectable content of cholesterol and triglycerides by sensitive assays.

A subject "very high density, ultra small, de-lipidated apolipoprotein B containing particle" can have an average particle diameter in the range of from approximately 7.1 nm to 22 nm, e.g., from about 7.1 nm to about 15 nm, from about 15 nm to about 18 nm, or from about 18 nm to about 22 nm. Thus, e.g., at least about 80%, at least about 85%, at least about 90%, at least about 95%, at least about 98%, or at least about 99%, of the particles in a population of "very high density, ultra small, de-lipidated apolipoprotein B containing particles" has an average particle diameter in a range of from about 7.1 nm to about 15 nm, from about 15 nm to about 18 nm, or from about 18 nm to about 22 nm.

A subject "very high density, ultra small, de-lipidated apolipoprotein B containing particle" can have a size in the range of from about 71 Å to about 220 Å, e.g., from about 71 Å to about 160 Å, from about 160 Å to about 175 Å, from about 175 Å to about 200 Å, from about 200 Å to about 210 Å, from about 210 Å to about 220 Å.

A subject "very high density, ultra small, de-lipidated apolipoprotein B containing particle" generally has a density greater than 1.21 g/mL, e.g., a subject "very high density, ultra small, de-lipidated apolipoprotein B containing particle" generally has a density of from about 1.21 g/mL to about 1.3 g/mL, or from about 1.3 g/mL to about 1.35 g/mL. Thus, e.g., at least about 80%, at least about 85%, at least about 90%, at least about 95%, at least about 98%, or at least about 99%, of the particles in a population of "very high density, ultra small de-lipidated apolipoprotein B containing particles" has a density of from about 1.21 g/mL to about 1.3 g/mL, or from about 1.3 g/mL to about 1.35 g/mL.

An isolated "very high density, ultra small, de-lipidated apolipoprotein B containing particle" of the present disclosure has substantially no lipid. For example, a subject "very high density, ultra small, de-lipidated apolipoprotein B containing particle" has substantially no cholesterol, e.g., a subject "very high density, ultra small, de-lipidated apolipoprotein B containing particle" will have less than about 10%, less than about 5%, less than about 3%, less than about 2%, less than about 1%, less than about 0.5%, less than about 0.2%, less than about 0.1%, or less than about 0.01%, by weight, cholesterol. In some cases, a subject "very high density, ultra small, de-lipidated apolipoprotein B containing particle" has no detectable cholesterol.

As another example, a subject "very high density, ultra small, de-lipidated apolipoprotein B containing particle" has substantially no triglycerides, e.g., a subject "very high density, ultra small, de-lipidated apolipoprotein B containing particle" will have less than about 10%, less than about 5%, less than about 3%, less than about 2%, less than about 1%, less than about 0.5%, less than about 0.2%, less than about 0.1%, or less than about 0.01%, by weight, triglycerides. In some cases, a subject "very high density, ultra small, de-lipidated apolipoprotein B containing particle" has no detectable triglycerides.

Apolipoprotein-B 100

Amino acid sequences of apoB-100 polypeptides are known in the art. For example, the following GenBank accession numbers provide amino acid sequences of apoB-100 polypeptides; 1) GenBank Accession No. NP_000375.2 (*Homo sapiens* apoB-100); 2) GenBank Accession No. XP_515323.2 (*Pan troglodytes* apoB-100); 3) GenBank Accession No. XP_001097500.1 (*Macaca mulatta* apoB-100); 4) GenBank Accession No. XP_001501729.1 (*Equus caballus* apoB-100); 5) GenBank Accession No. NP_033823.2 (*Mus musculus* apoB-100); and 6) GenBank Accession No. NP_062160.2 (*Rattus norvegicus* apoB-100).

In some embodiments, an apoB-100 polypeptide that is included in a subject "very high density, ultra small de-lipidated apolipoprotein B containing particle" comprises an amino acid sequence having at least about 85%, at least about 90%, at least about 95%, at least about 98%, at least about 99%, or 100%, amino acid sequence identity with amino acids 28-4563 of the amino acid sequence set forth in FIGS. 17A-D and SEQ ID NO:1.

Cytokeratin 8

Amino acid sequences of cytokeratin 8 polypeptides are known in the art. For example, the following GenBank accession numbers provide amino acid sequences of cytokeratin-8 polypeptides: 1) GenBank Accession No. AAA35763 (*Homo sapiens* cytokeratin 8); 2) GenBank Accession No. AAA19668.1 (*Rattus norvegicus* cytokeratin 8); 3) GenBank Accession No. AAI06155.1 (*Mus musculus* cytokeratin 8); 4) GenBank Accession No. AAI54778.1 (*Danio rerio* cytokeratin 8); and 5) GenBank Accession No. XP_002742819 (*Callithrix jacchus* cytokeratin 8).

In some embodiments, a cytokeratin-8 polypeptide that is included in a subject "very high density, ultra small, lipid depleted apolipoprotein B containing particle" comprises an amino acid sequence having at least about 85%, at least about 90%, at least about 95%, at least about 98%, at least about 99%, or 100%, amino acid sequence identity with the amino acid sequence set forth in FIG. 18 and SEQ ID NO:2.

Methods of Isolating a very high Density, Ultra Small, Lipid Depleted Apolipoprotein B Containing Particle The present disclosure provides a number of methods to isolate the ultra-small apo B containing particles which may contain cytokeratin 8. An immunoaffinity method can be used. For example anti-apoB antibody that is immobilized (e.g., on a column, a magnetic bead, and the like) can be contacted with a sample (e.g., plasma, such as human plasma) containing the particle, where the particle binds to the immobilizied anti-apoB antibody, forming an immobilized anti-apoB-particle complex. The particle in the immobilized complex can be eluted.

For example, Apo B antibody (antibody specific for apoB) was conjugated to the Dynabeads® M-280 Tosylactivated using manufacturer recommended procedure with slight modification such as replacing the bovine serum albumin (BSA) in buffer D with non-fat dry milk, replacing BSA in buffer E with Tween 20 and antibody conjugation temperature from 37° C. for 12-18 hours to 22-25° C. (room temperature) for 24 hours. Serum sample was diluted 1:200 in buffer D and incubated with apo B-specific monoclonal antibody conjugated to magnetic Dynabeads at 25° C. with continuous rocking/mixing for 30 minutes. At the end of the incubation period, the magnetic field was applied to the tubes, then supernatant was removed followed by 3 wash with phosphate buffer saline (PBS). Glycine buffer (pH 2.8) was used to elute/release the apo B particles from their respected antibody. Then the pH was immediately adjusted to around 7.5 with 2-2.5 µL of the 2.5 mmol NaOH. The eluted particles were dialyzed over night against 25 mmol ammonium acetate before analysis with ion mobility (IM), see FIG. 1. Furthermore, the eluted particles were assayed using an enzyme-linked immunosorbent assay (ELISA) to estimate the recovery of this method.

Figure 2:
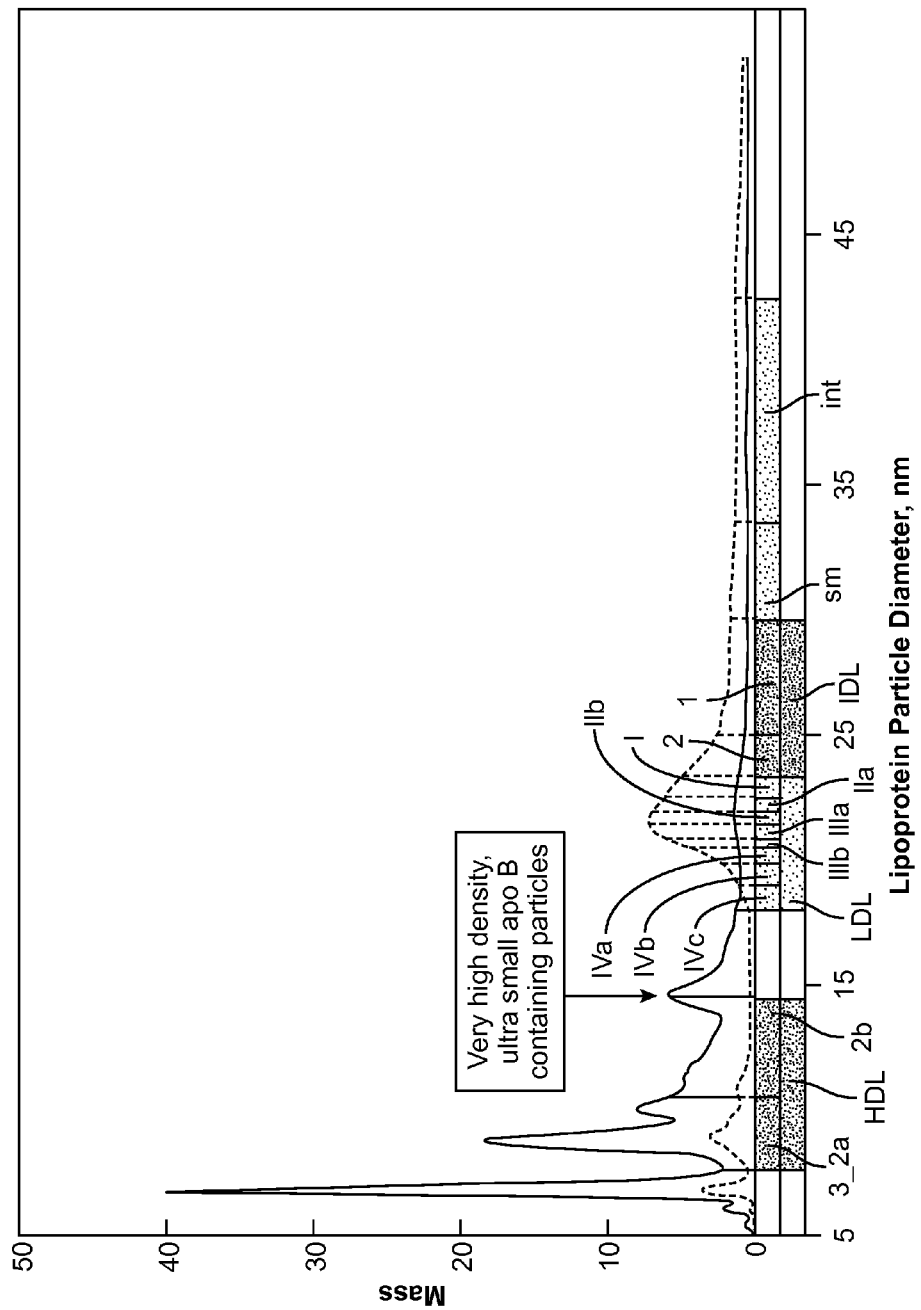
FIG. 2 depicts ion mobility analysis of the d<1.21 g/ml ultracentrifugal fraction of plasma (blue) and the d>1.21 g/ml ultracentrifugal fraction of plasma (black) from a representative individual.

The density gradient is one of the methods used. The density of the plasma was adjusted to 1.21 g/mL (by adding 1.91 gram NaBr to 6.503 mL plasma) and to 1.25 g/L (by adding 2.294 gram NaBr to 6.4 mL plasma). After completely dissolving the NaBr into the plasma, 6 mL was taken and added to the ultracentrifuge tubes, and then 6 µL 10 mmol trolox (6-hydroxy-2,5,7,8-tetramethylchroman-2-carboxylic acid) was added to each tube to prevent oxidation of lipoproteins. Ultracentrifugation was carried out at 40,000 rpm (115,046 g force) and 15° C. for 24 hours. At the end of the ultracentrifugation, the tubes were carefully removed and the top 1.5 mL was harvested from the all tubes. The top and bottom fractions were dialyzed against 25 mmol ammonium acetate for approximately 24 hours at 4° C. Following the dialysis of the plasma fractions, Ion Mobility was used to measure particles size (FIG. 2). Also the top and bottom density fractions were subject to above described immunoassay isolation procedure to isolate the very high density ultra-small dense apo B containing particles (see FIG. 3). In addition, the concentration of apo B was measured by ELISA assay using monoclonal specific antibody (see, e.g., Table 1, below, for apo B ultracentrifugation recovery by ELISA).

The present disclosure also provides a gradient gel electrophoresis method of isolating a very high density, ultra small apolipoprotein B containing particle described above. A subject method generally involves applying a sample (e.g., a plasma sample) comprising the very high density, ultra small apolipoprotein B containing particles as described above, on a 2-14% non-denaturing gradient polyacrylamide gel; separating the components of the sample on the gel by applying increasing voltage to the gel; and collecting fractions that advance beyond an LDL-IV standard band in the gel.

Pre-stained lipoprotein standards can be run alongside the sample, to provide an indication as to where to elute the sample. Suitable standards include: Lp(a); Large LDL; LDL-III; and LDL-IV. "Lp(a)" refers to biological particles consisting of LDL covalently attached to the protein lipoprotein A.

For example, a plasma (e.g., human plasma) sample is applied to a slot in a 2-14% non-denaturing gradient polyacrylamide gel; and pre-stained standard lipoproteins (e.g., Lp(a); Large LDL; LDL-III; and LDL-IV) are applied to sample application slots on either side of the plasma application slot. The gel can be run at 125 V 12-18 hours, i.e., 125 volts can be applied to the gel for 12-18 hours. Alternatively, the following voltage gradient can be applied: 20V for 15 minutes, 40V for 15 minutes, 60V for 15 minutes, 80V for 15 minutes, and 125V for 15 minutes, for a total of 1 hour 15 minutes; and the voltage gradient re-applied continuously over the course of 12 hours. After application of the voltage for 12-18 hours, a portion of the gel that is in a position beyond (toward the cathode side of the gel) the position of the LDL-IV band is excised, creating a trough (FIG. 4); the trough is filled with buffer; and voltage (250V) is applied to the gel for approximately 30-60 minutes to allow components of the sample to enter the buffer-filled trough, forming an elution sample. The elution sample is then analyzed for the presence of the very high density, ultra small apolipoprotein B containing particles. Any convenient method, e.g., ion mobility analysis, can be used to test the "very high density, ultra small lipid depleted apolipoprotein B containing particle" present in the elution sample. Ion mobility analysis is described in, e.g., U.S. Patent Publication No. 2010/0213061. The presence in the particle of apoB-100 and cytokeratin 8 can be detected using antibodies specific for these components.

Detection Methods

The present disclosure provides various detection methods involving detection of a very high density, ultra small, lipid depleted apolipoprotein B containing particles. The present disclosure provides methods for detecting a very high density, ultra small, lipid depleted apolipoprotein B containing particle, as described herein, in a biological sample obtained from an individual. The methods generally involve contacting the biological sample with an antibody specific for apoB 100 and/or an antibody specific for cytokeratin-8; and detecting binding of the antibody to molecules in the sample. A subject isolated very high density, ultra small, lipid depleted apolipoprotein B containing particle can be used as a positive control in a subject detection method.

The presence in the biological sample of an amount of the very high density, ultra small, lipid depleted apolipoprotein B containing particle and/or cytokeratin 8 that is higher than a normal control amount can indicate that the individual from whom the biological sample was obtained has, or is at higher risk than the general population of developing, a disorder such as cardiovascular disease, atherosclerosis, myocardial infarction, or atherosclerotic plaque rupture, or is at risk of atherosclerotic plaque rupture. In some cases, the level of the very high density, ultra small, lipid depleted apolipoprotein B containing particle and/or cytokeratin 8 can provide an indication of the individual's prognosis following placement in the individual of a stent. In some cases, the level of the very high density, ultra small, lipid depleted apolipoprotein B containing particle and/or cytokeratin 8 can provide an indication of the individual's prognosis following coronary artery bypass graft surgery (CABG).

The present disclosure provides diagnostic assays for determining whether an individual has cardiovascular disease (CVD); assays for assessing an individual's response to therapy for a CVD or other drug treatment; and prognostic assays for determining the risk that an individual will develop CVD. A subject isolated very high density, ultra small, lipid depleted apolipoprotein B containing particle can be used as a positive control in a subject detection method. A subject isolated very high density, ultra small, lipid depleted apolipoprotein B containing particle can be used to generate a standard curve, for use in a subject detection method, e.g., where the detection is qualitative.

Detecting an Ultra-small Apo B Containing Particles

A very high density, ultra small, lipid depleted apolipoprotein B containing particle as described above can be detected in a biological sample (e.g., blood, or a blood fraction such as serum or plasma). A very high density, ultra small, lipid depleted apolipoprotein B containing particle as described above, can be detected using, e.g., antibody specific for apoB and antibody specific for cytokeratin 8. An antibody specific for a component (e.g., an antibody specific for apoB-100; an antibody specific for cytokeratin 8) can comprise a detectable label. Suitable detectable labels include any composition detectable by ion Mobility, spectroscopic, photochemical, biochemical, immunochemical, electrical, optical, or chemical means. Suitable detectable labels include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), a radiolabel (e.g., $^3H$, $^{125}I$, $^{35}S$, $^{14}C$, or $^{32}P$), an enzyme (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

An antibody specific for a component (e.g., an antibody specific for apoB-100; an antibody specific for cytokeratin 8) can be immobilized on a on a solid support. Suitable supports are well known in the art and comprise, inter alia, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc.

In some cases, the average particle diameter size and the mass of the particle are determined following detection of the particle. The average particle diameter and mass of the particle can be determined using ion mobility analysis. See, e.g., U.S. Patent Publication No. 2010/0213061. Non-denaturing polyacrylamide gradient gel electrophoresis (see, U.S. Pat. No. 5,925,229). Agarose gel electrophoresis. Nuclear Magnetic Resonance (NMR), see U.S. Patent No. 20110004453. Density gradient ultracentrifugation. Electron microscope. Any method cable to count and measuring particles size not listed here.

The substantial lack of triglycerides and cholesterol can be determined using standard assays for these compounds. For example, methods involving use of enzymatic hydrolysis of triglycerides to glycerol and free fatty acids, followed by either colorimetric or fluorometric measurement of the glycerol released, can be used. For standard assays for triglycerides see, e.g., Bucolo and David (1973) *Clin. Chem.*

19:476; Fossati and Prencipe (1982) *Clin. Chem.* 28:2077; McGowan et al. (1983) *Clin. Chem.* 29:538; and Mendez et al. (1986) *Anal. Biochem.* 156:386. Various colorimetric and fluorometric assays for cholesterol are known in the art; and any such assay method can be used to determine substantial lack of cholesterol in an apoB/apoA-I particle as described herein. See, e.g., Kishi et al. (2002) *Clin. Chem.* 48:737, for an example of an assay for cholesterol.

The detection can be quantitative or qualitative. In some embodiments, e.g., where quantitative detection is desired, a standard curve using known amounts (e.g., 1 ng, 10 ng, 50 ng, 100 ng, 1 µg, 10 g, 50 µg, 100 µg, etc.) of a subject very high density ultra-small apo B containing particles is used.

Assessing Risk of CVD

The present disclosure method for assessing risk of CVD in an individual, the method comprising: detecting (e.g., measuring, determining, or assessing) a level of a very high density, ultra small, lipid-depleted apo B containing particle as described above in a biological sample from the individual; and assessing the risk based on the detected level of the particle. A level of the very high density, ultra small, lipid depleted apo B containing particle that is higher than a normal control level indicates that the individual has an increased risk of CVD. For example, a level of the "very high density, ultra small, lipid depleted apo B containing particle" that is at least 15% higher, at least 25% higher, at least 50% higher, at least 75% higher, at least 2-fold higher, at least 5-fold higher, or greater than 5-fold higher, than a normal control level indicates that the individual has an increased risk of CVD. CVD includes atherosclerosis, coronary artery disease (which may result in myocardial infarction), angina, stroke, hypertension, and heart failure. In some instances, the individual (e.g., a human) exhibits at least one clinical symptom or sign of cardiovascular disease.

A subject method of assessing risk of CVD can involve use of a subject kit (as described below), where the kit can include a positive control (e.g., a purified very high density ultra-small apo B containing particle, as described above) and/or components for generating a standard curve (e.g., a subject isolated very high density ultra-small apo B containing particle in defined amounts, e.g., 1 ng, 10 ng, 50 ng, 100 ng, 1 µg, 10 µg, 50 µg, 100 µg, etc.). For example, the level of the very high density, ultra small, lipid depleted apo B containing particle can be determined by comparison to a standard curve generated using a subject isolated very high density ultra-small apo B containing particle in defined amounts.

Based on a subject detection method, a certain therapeutic regimen may be recommended by a physician or other qualified medical personnel. For example, where the outcome of subject detection method indicates that the individual has an increased risk, compared to a healthy individual who has no signs of CVD, of developing CVD, a recommendation as to pharmaceutical intervention, diet alteration, exercise regimen, and the like, may be made.

In some cases, a subject method of assessing risk of CVD can further include communicating to the individual from whom the biological sample was obtained (in which biological sample the level of the very high density ultra-small apo B containing particle was detected) the results of the assessment and/or suggested treatment regimens. Thus, in some embodiments, a subject method comprises detecting a level of a very high density, ultra small, lipid depleted apo B containing particle as described above in a biological sample from the individual; assessing the risk that the individual has or will develop CVD based on the detected level; and communicating a recommended treatment regimen to the individual. The recommended treatment regimen can be based on a therapy decision tree that sets forth various treatment options, depending on the results of the subject method, and optionally other patient information (e.g., results of other tests, such as other tests for CVD; patient medical history; any prior or ongoing treatment the patient is undergoing; etc.).

In some embodiments, a subject method of assessing risk of CVD can further include treating the individual for CVD. For example, an individual determined to be a higher risk of CVD than the general population can be treated with a blood pressure-lowering drug (e.g., a diuretic; a beta blocker), an anti-coagulant drug, or a cholesterol-lowering drug. For example, an individual determined to be a higher risk of CVD than the general population can be treated with: 1) a diuretic, e.g., a thiazide diuretic; 2) a beta blocker (e.g., Sectral (acebutolol); Zebeta (bisoprolol); Bevibloc (esmolol); Inderal (propranolol); Tenormin (atenolol); Normodyne (labetalol); Coreg (carvedilol); Lopressor (metoprolol)); 3) an anti-coagulant such as Coumadin (warfarin), Heparin, Lovenox, or Fragmin; or 4) a cholesterol-lowering drug such as a HMG-CoA reductase inhibitor (a statin) (e.g., atorvastatin (Lipitor), fluvastatin (Lescol), lovastatin (Mevacor), pitavastatin (Pitava), pravastatin (Pravachol), rosuvastatin (Crestor), simvastatin (Zocor)), or a fibrate (e.g., gemfibrozil (Lopid), fenofibrate (Tricor), or fenofibric acid (Trilipix).

A subject method of assessing risk of CVD can further include generating a report that provides an indication of the risk that the individual will develop CVD. A "report," as described herein, is an electronic or tangible document that includes report elements that provide information of interest relating to a likelihood assessment and its results. A subject report includes at least a likelihood assessment, e.g., an indication as to the risk that an individual will develop CVD. A subject report can be completely or partially electronically generated, e.g., presented on an electronic display (e.g., computer monitor). A report can further include one or more of: 1) information regarding the testing facility; 2) service provider information; 3) patient data; 4) sample data; 5) an interpretive report, which can include various information including: a) indication; b) test data, where test data can include the level of very high density, ultra small, lipid depleted apo B containing particles and a normal control level of very high density, ultra small, lipid depleted apo B containing particles and 6) other features.

Thus, in some embodiments, the methods of the present disclosure further include generating a report that includes information regarding the patient's likely clinical outcome, e.g. risk of CVD. For example, the methods disclosed herein can further include a step of generating or outputting a report providing the results of a subject risk assessment, which report can be provided in the form of an electronic medium (e.g., an electronic display on a computer monitor), or in the form of a tangible medium (e.g., a report printed on paper or other tangible medium).

Assessing Efficacy of Treatment

The present disclosure provides a method of assessing the efficacy of a treatment for a cardiovascular disease in an individual. In some cases, the method comprises: a) analyzing the level of a very high density, ultra small, lipid depleted apo B containing particles (as described above) in a biological sample obtained from the individual following the treatment; and b) comparing the post-treatment level to a pre-treatment level. A post-treatment level that is lower than the pre-treatment level indicates that the treatment was efficacious.

In some cases, a method of assessing efficacy of therapy involves analyzing the level of very high density, ultra small, lipid depleted apo B containing particles (as described above) in a biological sample obtained from an individual at a first time point during treatment for a CVD; analyzing the level of very high density, ultra small, lipid depleted apo B containing particles (as described above) in a biological sample obtained from an individual at a second time point (where the second time point is later than the first time point) during treatment for a CVD; and comparing the level from the first and second time points. A level at the second time point that is lower than the level at the first time point indicates that the treatment was efficacious. The second time point can be from one day to one week, from one week to one month, from one month to three months, from three months to six months, or more than six months, later than the first time point.

Determining Risk of Mortality

The present disclosure provides a method of determining the risk of mortality due to a CVD in an individual. The method comprises detecting a level of very high density, ultra small, lipid depleted apo B containing particles (as described above) in a biological sample from the individual. A level of the particle that is higher than a normal control level indicates that the individual has an increased risk of mortality due to a CVD.

Kits

The present disclosure provides a kit (e.g., a test kit) for use in carrying out a subject detection method. A subject kit includes an antibody specific for apoB-100 and an antibody specific for cytokeratin 8. The antibodies can be in separate containers. The antibodies can be immobilized on a solid support. The antibodies can be detectably labeled.

The antibodies can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

In some embodiments, a subject kit includes an antibody specific for apoB-100 and an antibody specific for cytokeratin 8, where each antibody is immobilized on a solid support, such as a test strip.

An antibody included in a subject kit will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3H$, $^{125}I$, $^{35}S$, $^{14}C$, or $^{32}P$), enzymes (e.g., horse radish peroxidase, alkaline phosphatase, luciferase, and others commonly used in an ELISA), and colorimetric labels such as colloidal gold or colored glass or plastic (e.g. polystyrene, polypropylene, latex, etc.) beads.

A subject kit can further include reagents for detecting triglycerides; reagents for detecting cholesterol; etc. Other optional components of the kit include: a buffer; a protease inhibitor; a detectable label; etc. The various components of the kit may be present in separate containers or certain compatible components may be pre-combined into a single container, as desired.

In addition to above-mentioned components, a subject kit can include positive controls (e.g., a purified very high density ultra-small apo B containing particle); and/or components for generating a standard curve (e.g., a subject isolated very high density ultra-small apo B containing particles in defined amounts, e.g., 1 ng, 10 ng, 50 ng, 100 ng, 1 μg, 10 μg, 50 μg, 100 μg, etc.).

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Isolation and Characterization of Very High Density, Ultra Small, Lipid Depleted apo B Containing Particles Materials and Methods Materials Monoclonal apo B antibody M-035 (cat#H45640M, concentration 4.61 mg/mL, lot#7821) and M-036

(Cat#H45161M, concentration 2.1 mg/mL, lot#4A03107) from Meridian Life Science, Saco, Me. 04072, USA. Dynabeads M-280 Tosylactivated magnetic beads cat#142-04 from Invitrogen, Carlsbad, Calif. 92008, USA.

Polyacrylamide gradient gels (2-14%), with 18 sample loading lanes, were produced locally at the Children's Hospital Oakland Research Institute (CHORI), Oakland, Calif. 94609, USA. Electrophoresis chamber with power supply and cooling device was from Pharmacia Company, Stockholm, Sweden. Concentrated electrophoresis buffer was made in-house according to a standard operating procedure; 217.93 grams (gm) trizma base (Tris-hydroxymethyl aminomethane), 98.88 gm boric acid, 20.20 gm di-sodium EDTA in 4000 mL double deionized water. The working solution was made by diluting the concentrated buffer 1 in 5 (600 ml concentrated buffer+2400 double deionized water).

Sudan black stain was from Beckman-Coulter, Fullerton, Calif., USA. Lipoprotein particle size calibrator or quality control (LPCAL: AE/AG) was made in-house, and provided the following range of particle sizes: 315, 275.8, 248.7, and 225.2 Å. Sample application comb was from Pharmacia, Stockholm, Sweden. Centricon-10 (cat#4206) 2 ml-concentrator was from Amicon, Billerica, Mass., USA.

Other reagents and product were obtained from the following sources: 1) Coomassie blue (cat#6104-58-1) (Sigma, St. Louis, Mo., USA); 2) Airborne ion mobility analyzer (TSI incorporation, Minn., USA); 3) Cholesterol reagent (cat#E33940), (Polestar Laboratory, Escondido, Calif., USA); 4) Free Glycerol Reagent A (Sigma, cat. No. F6428, 40 ml); 5) Triglyceride Reagent B (Sigma, cat. No. T2449, 10 ml); and 6) Bradford protein assay (Bio-Rad, cat. No. #500-0202, Hercules, Calif. 94547).

A monoclonal specific antibody against apoB-100, (catalogue No. K90086P), and horseradish peroxidase (HRP) conjugated secondary (anti-IgG) antibody, were obtained from Biodesign International, a division of Meridian Life Science Inc, Saco, Me. 04072, USA.

Additional reagents and products were obtained from the following sources: 1) Super-signal developing reagent kit, (catalogue No. 34096), from Pierce, Rockford, Ill. 61105, USA; 2) X-ray film, (catalogue No. EK8FL), Belgium; 3) X-ray film developing equipment from Kodak, Rochester, N.Y.; 4) Bovine albumin (>99% purity), (catalogue No. A-6003) from Sigma, St. Louis, Mo., USA; 5) Glycine, (catalogue No. G7126) from Sigma; 6) Methanol, (catalogue No. M1775) from Sigma-Aldrich, St Louis, Mo., USA; 7) Trizma-base (Hydroxymethyl aminomethane), (catalogue No. T1503) from Sigma-Aldrich; 8) sodium dodecyl sulfate (SDS) gel 3-8% and 4-20% (catalogue No. EC60385) from Invitrogen, Carlsbad, Calif. 92008, USA; 9) SDS reducing agent (catalogue No. NP0009) from Invitrogen; 10) SDS tracking dye (catalogue No. NP0007) from Invitrogen; 11) SDS running buffer, (catalogue No. NP0001) from Invitrogen; 12) Antioxidant, (catalogue No. NP0005) from Invitrogen; 13) Nitrocellulose transfer membrane, (catalogue No. 13849) from Bio-Rad, Hercules, Calif., 94547, USA; 14) Tween-20 detergent, (catalogue No. P1379) from Sigma-Aldrich; 15) Phosphate buffered saline (PBS) made according to the laboratory standard operating protocol, CHORI, Oakland, Calif., USA; 17) Pre-stained proteins molecular weight standard (10-250 KDA), (catalogue No. 161-0375) from Bio-Rad, Hercules, Calif., USA and 27-180 KDA from Sigma, catalogue #MW-SDS-Blue; 18) Unstained proteins molecular weight (40-500 KDA) standard, (catalogue No. LC5688) from Invitrogen; 19) ApoB-100 and apoB-48 standard prepared in-house; 20) Brilliant Blue G (Coomassie blue) stain, (catalogue No. B0770) from Sigma; 21) SDS gels de-staining solution made according to the laboratory standard operating protocol; 22) Polyclonal specific antibody against cytokeratin 8, (catalogue No. RB-9095-PO) from Labvission, Fremont, Calif., USA; and 23) Cytokeratin 8 positive control, (catalogue No. RB-9095-PCL) from Labvission, Fremont, Calif., USA.

Methods

Separation of very high Density, Ultra Small, Lipid Depleted apo B Containing Particles by Immunoaffinity Apo B was conjugated to the Dynabeads® M-280 Tosylactivated using manufacturer recommended procedure with slight modification such as replacing the bovine serum albumin (BSA) in buffer D with non-fat dry milk powder, replacing BSA in buffer E with Tween 20 and antibody conjugation temperature from 37° C. for 12-18 hours to 22-25° C. for 24 hours. Samples were diluted 1:200 in buffer D and incubated with beads conjugated with apo B-specific antibody at 25° C. with continuous rocking for 30 minutes. At the end of the incubation period, a magnetic field was applied to the tubes, then the supernatant was removed, followed by 3 washes with phosphate buffer saline (PBS). Glycine buffer (pH 2.8) was used to elute the apo B particles. Then the pH was immediately adjusted to around 7.0 with 2 µL of the 2.5 mmol NaOH. The eluted particles were dialyzed over night against 25 mmol ammonium acetate before analysis by ion mobility.

Isolation of very high Density, Ultra Small, Lipid Depleted apoB Containing Particles by Ultracentrifugation Plasma density adjustment: The density of the plasma was adjusted to 1.21 g/mL (by adding 1.91 gram NaBr to 6.503 mL plasma) and to 1.25 g/L (by adding 2.294 gram NaBr to 6.4 mL plasma). After completely dissolving NaBr into the plasma, 6 mL was taken and added to the ultracentrifuge tubes, then 6 µL 10 mmol trolox was added to each tube to prevent lipoproteins oxidation. Mock solution density adjustment: The density of the mock solution was adjusted to 1.21 g/mL (by adding 1.91 gram NaBr to 6.503 mL plasma) and to 1.25 g/L (by adding 2.294 gram NaBr to 6.4 mL plasma). After complete dissolution of NaBr into the mock solution, 6 mL was taken and added to the ultracentrifuge tubes, then 6 µL 10 mmol trolox was added to each tubs for reason of treating these tubes equally to the plasma tubes. These tubes served as balance in the ultracentrifuge and also for density verification for the plasma tubes. Ultracentrifugation was carried out at 40,000 rpm (average 115,046 g force), at 15° C. for 24 hours. At the end of the ultracentrifugation, the tubes were carefully removed and the top 1.5 mL was harvested from the all tubes (plasma and mock solution). Densities of the top and bottom fractions of the mock solution tubes were measured by the densitometer. The top and bottom fractions were dialyzed against 25 mmol ammonium acetate for approximately 24 hours at 4° C. Following the dialysis of the plasma fractions, ion mobility was used to measure particle size. In addition, the concentration of apoB was measured by ELISA assay using monoclonal specific antibody.

Isolation of very high Density, Ultra Small, Lipid-Depleted apo B Containing Particles by Gradient Gel Electrophoresis (GGE)

A pre-staining lipoprotein standard with known peak particles size (Å) was prepared as follows prior to carrying out the procedure: Sudan black 'Lipostain' (Beckman Coulter) was added to the lipoprotein standard to make a 4% (v/v) solution (4 µLipostain+96 µl lipoprotein standard). This was then incubated overnight (~12 h) and was used within one week.

A pre-staining lipoprotein standard with known peak particles size (Å) was prepared as follows prior to carrying out the procedure: Sudan black 'Lipostain' (Beckman Coulter) was added to the lipoprotein standard to make a 4% (v/v) solution (4 µLipostain+96 µl lipoprotein standard). This was then incubated overnight (~12 h) and was used within one week.

The electrophoresis buffer was cooled to a temperature between 8-16° C. The gel (2-14%) was pre-electrophoresed at 125 volts for at least 30 minutes to remove any particulates and to condition the gel with electrophoresis buffer. A pre-stained lipoprotein standard with known particle size was applied (10 µL) to lanes 1, 2, 17 and 18. Plasma samples (10 µL) were applied to lanes 3 through 16. Electrophoresis was carried for 15 minute intervals at 20, 40, 60, and 80V, and at 125V overnight (12 hours).

A scalpel or a razor blade was used to remove the top section of the gel (~1-3 mm) to remove any proteins or albumin that might have been trapped with the VLDL fraction in this part of the gel. The gel was then re-loaded using fresh electrophoresis buffer and electrophoresis was carried out at 250V for an additional 2 hours.

At the end of the 2 hours, a scalpel or razor blade and a ruler was used to excise the gel and create a window below the LDL-IV band (225 Å) with an approximate width of 0.5 cm. A length of about 0.5 cm was left on the side of the window to hold the upper and lower parts of the gel together (see FIG. 4). The window was filled with 1× Trizma Borate EDTA (TBE) buffer and was covered with a dialysis membrane to prevent buffer leakage.

The gel cassette was then re-assembled and re-inserted into the upper electrophoresis chamber, and electrophoresis was continued at 250 volts for 45 minutes to collect fraction 1. Then the gel cassette was opened to collect the first fraction by aspiration using plastic transfer pipette. This aspiration was repeated a few times to ensure that all particles belonging to that fraction were collected.

The cassette was re-assembled and re-loaded again into the GGE chamber and electrophoresis was continued at 250 volts for intervals of 1 hour until all of the LDL fractions of interest had been separated and collected. The volume of each fraction was approximately 500 µl from each gel and the total volume from 4 gels was 2 mL.

The collected fractions were then concentrated by centrifugation at 7,000 rpm for 60 minutes at a temperature of 4° C. using the 2 ml concentrator Centricon-10 to reduce the volume to approximately 500 µl (4× concentration). To verify the uniformity of the final collected fractions, they were separated a second time by electrophoresis on a new 2-14% gradient gel, and by an ion mobility analyzer, for the measurements of their particles size diameter.

Ion Mobility (IM)

An ion mobility analyzer was used as an additional tool to test the eluted lipoprotein particles as described by Caulfield et al 2008.

Molecular Weight Determination of Proteins by SDS-PAGE

SDS polyacrylamide gel electrophoresis (SDS-PAGE) was used to identify proteins associated with the LDL-IV fraction according to their molecular weight. First the protein concentration was measured with Bradford protein assay (0.158 µg/mL; assay sensitivity 0.125-2.0 mg/ml) then the proteins of interest were separated and stained on SDS-PAGE as described by the kit manufacturer (Invitrogen, Calif., USA).

Protein Transfer Procedure

Following the separation of proteins by SDS-PAGE as described above, the proteins were transferred to a nitrocellulose membrane for immunoblotting as described by the kit manufacturer (Invitrogen, Calif., USA.

Immunoblotting

The manufacturer procedure was modified/optimized and carried out as follows.

Bovine Serum Albumin (BSA) (3%) was made with PBS buffer, then 25 µl of Tween-20 was added to 50 ml of 3% bovine albumin (0.05%) and the membrane was incubated with gentle shaking at room temperature or overnight at 4° C.

The membrane was incubated, with shaking, with an apoB-specific primary antibody diluted 1:10,000 with 3% BSA containing Tween-20 at a concentration of 0.05% at 300 revolutions for 2 hours at RT or overnight in the cold room. The 0.3% BSA containing 0.05% Tween-20 was used as a washing buffer to wash the membrane on three occasions, at 10 minutes for each wash, to remove all non-specific binding of antibodies. The membrane was incubated with secondary apoB HRP conjugated antibody (diluted 1:5000) for 1 hour at room temperature (RT). The membrane was washed 5 times, with shaking, using the washing buffer described above, at 300 revolutions for 10 minutes for each wash to remove any non-specific binding.

The membrane was developed using the super signal reagent, prepared by adding 1 ml Reagent One to 1 ml Reagent Two in 8 ml distilled water. The membrane was then soaked in the super signal reagent for 2-5 minutes, after which, the developed membrane was placed between two layers of clear thin plastic. The membrane was exposed to x-ray film for 10, 20, 30, 60, and 90 seconds. The exposed films were then developed and examined.

Determination of Molecular Mass of the 52 kDa band by Mass Spectrometry (MS)

Mass spectrometry was performed at Stanford University, Palo Alto, Calif., USA, according to their laboratory standard operating procedure (Shevchenko et al, 1996, 2007). The very high density, ultra small, lipid depleted apo B containing particles were separated and stained after SDS-PAGE as described above and in-gel trypsin digestion and protein analysis of the ≈52 kDa band by MS was performed.

Results

The immunoaffinity procedure was employed using monoclonal apo B antibody to isolate very high density, ultra small, lipid depleted apo B containing particles directly from plasma. The isolated particles were analyzed by ion Mobility as shown in FIG. 1.

Figure 3:
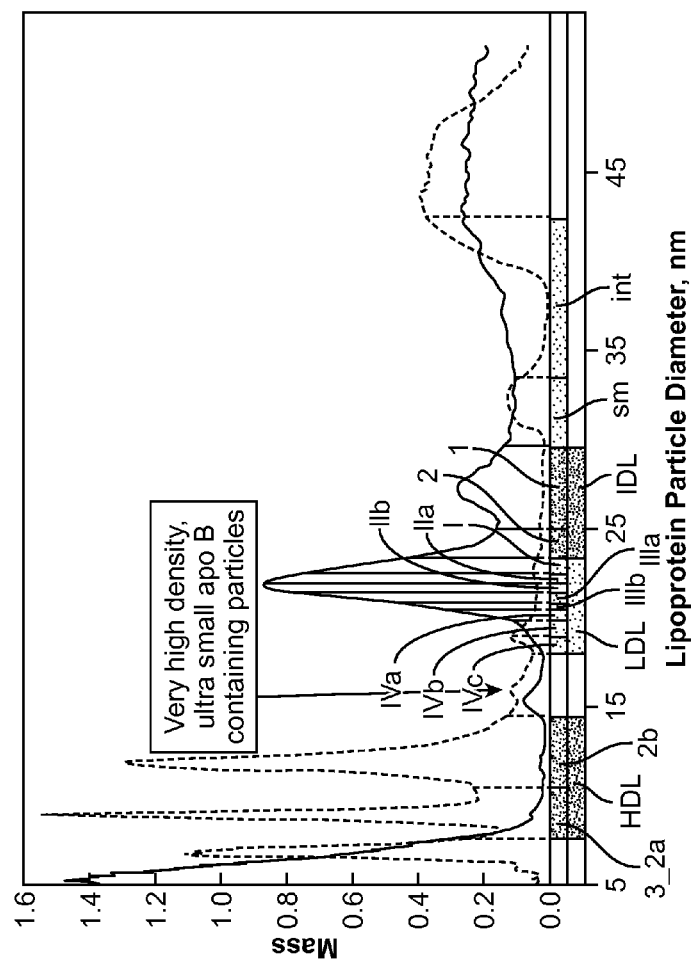
FIG. 3 depicts ion mobility analysis of the apoB-containing lipoproteins isolated from the ultracentrifugal fractions described in FIG. 2 using a specific anti-apoB antibody conjugated to magnetic beads.

Following the ultracentrifugal separation, dialysis and appropriate dilution of the top and bottom fractions of the very high density solution containing the sample of interest, the following results were obtained by ion Mobility as shown in FIG. 2. Also the immunoaffinity procedure was used to isolated apo B containing particles from the top 1.5 mL of the 1.25 g/mL density (black line) and from the bottom 4.5 mL of the 1.25 g/mL density (blue line) ultra-centrifuged sample and then the eluted particles were analyzed by ion Mobility as shown in FIG. 3. The ELISA results for apoB in the top and bottom density fractions are shown in Table 1.

TABLE 1

| Density 1.21 g/mL | Dilution factor | Concentration factor | apo B concentration | final apo B result |
|---|---|---|---|---|
| Top fraction | 1.08 | 4 | 219.6 | 59.3 |
| Bottom fraction1.08 | 1.3 | 7.2 | 6.0 | |
| Top + Bottom | | | | 65.3 |

TABLE 1-continued

| Density 1.21 g/mL | Dilution factor | Concentration factor | apo B concentration | final apo B result |
|---|---|---|---|---|
| Original Plasma | N/A | N/A | 80 | 80 |
| Recovery | | | | 82% |

Table 2: apo B recovery calculation in comparison to the original plasma concentration; some losses may be attributed to adhesion to the ultracentrifuge tube.

FIG. 1. IM profile showing the total apo B containing particles following immunoaffinity isolation (directly from the plasma) using monoclonal apo B antibody.

FIG. 2. IM profile showing LDL and HDL (blue line) isolated from the 1.5 mL top fraction of 1.21 g/mL and the very high density ultra small particles (black line) isolated from the 4.5 mL bottom 1.21 g/mL.

FIG. 3. IM profile showing immunoaffinity isolated apo B containing particles from the top 1.5 mL of the 1.25 g/mL density (black line) and from the bottom 4.5 mL of the 1.25 g/mL density (blue line) ultracentrifuged sample.

Since the gel elution method released the smaller and denser particles first, the fraction numbers were inversely related to LDL fractions as defined by increasing density in the ultracentrifugation i.e. I to IV. The gel elution fractions start at 1, 2, 3, 4, and 5, moving from smaller and denser particles to the larger and more buoyant particles, in which fraction 1 corresponds to the very high density, ultra small, lipid depleted apo B containing particles) (F1), fraction 2 to LDL-IV (F2), fraction 3 to LDL-III (F3), while fractions 4 and 5 correspond to the larger LDL's (F4 and F5).

Ion Mobility Analysis

Figure 5:
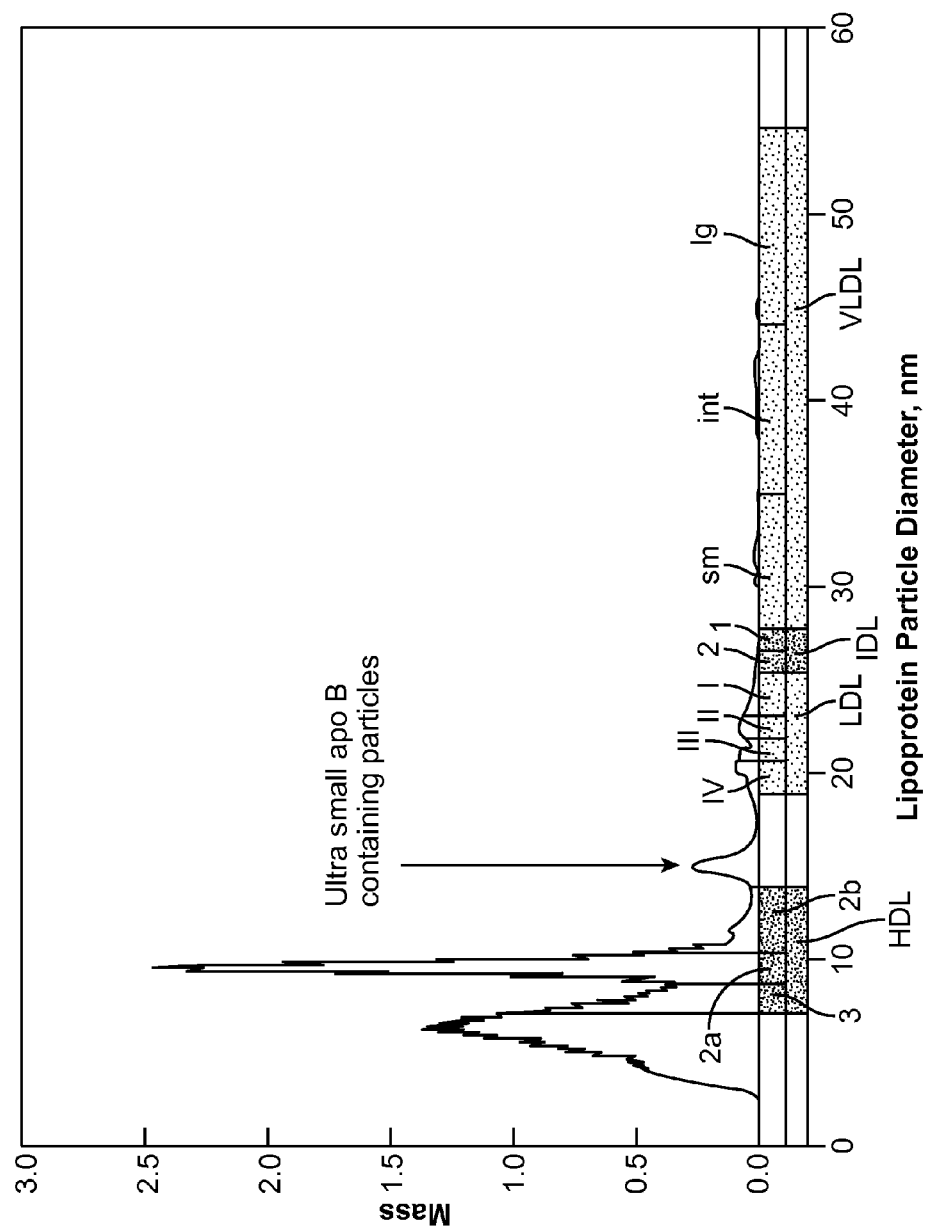
FIG. 5 depicts ion mobility analysis of particles isolated by electrophoresis in fraction 1 from the elution window shown in FIG. 4.
Figure 6:
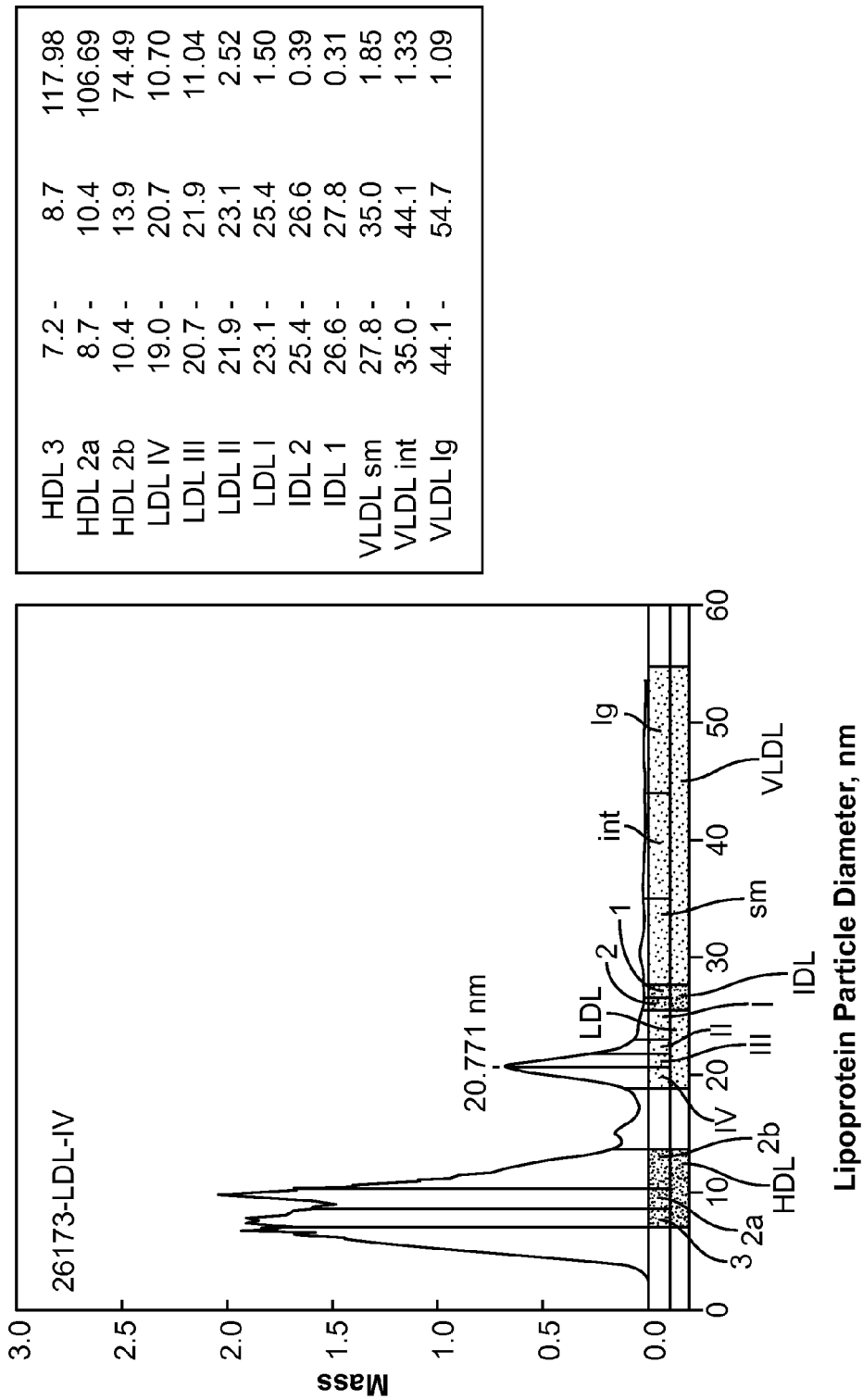
FIG. 6 depicts ion mobility analysis of particles isolated by electrophoresis in fraction 2 from the elution window shown in FIG. 4.
Figure 7:
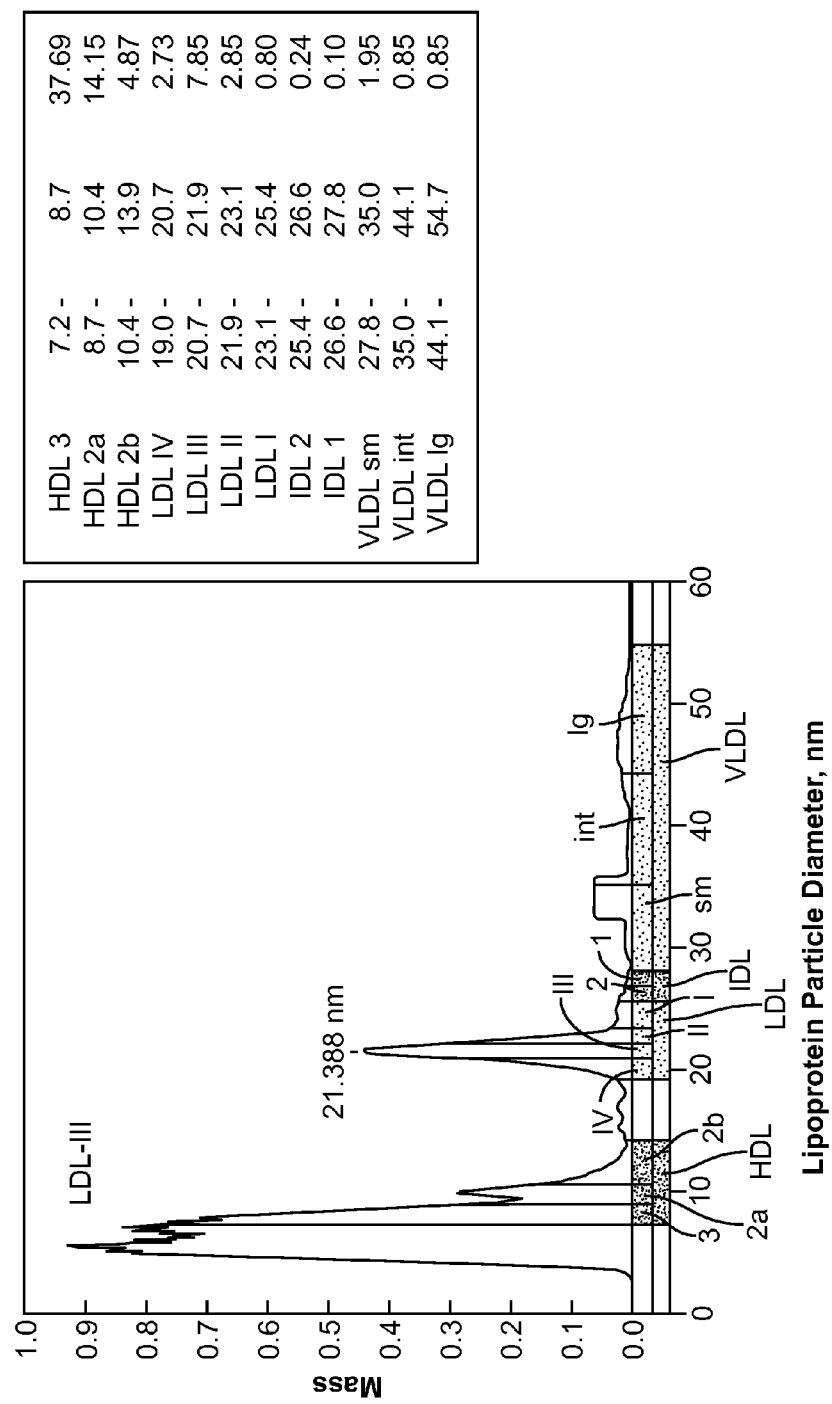
FIG. 7 ion mobility analysis of particles isolated by electrophoresis in fraction 3 from the elution window shown in FIG. 4.

The characteristics of the particles in the separated fractions, namely very high density, ultra small, lipid depleted apo B containing particles), LDL-IV and LDL-III, were confirmed by ion mobility analysis as shown in FIG. 5, FIG. 6, and FIG. 7.

Figure 4:
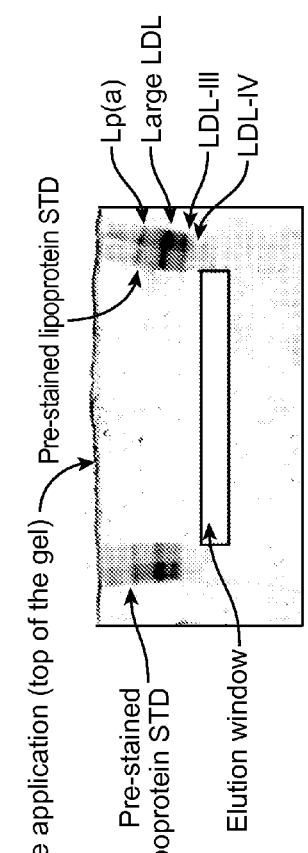
FIG. 4 displays a 2-14% gradient polyacrylamide gel, showing the elution window with pre-stained lipoprotein standards.

FIG. 5 depicts ion mobility analysis of particles isolated by electrophoresis in fraction 1 from the elution window shown in FIG. 4.

FIG. 6 depicts ion mobility analysis of particles isolated by electrophoresis in fraction 2 from the elution window shown in FIG. 4.

FIG. 7 ion mobility analysis of particles isolated by electrophoresis in fraction 3 from the elution window shown in FIG. 4.

Fractions on 2-14% Gradient Gels

Figure 8:
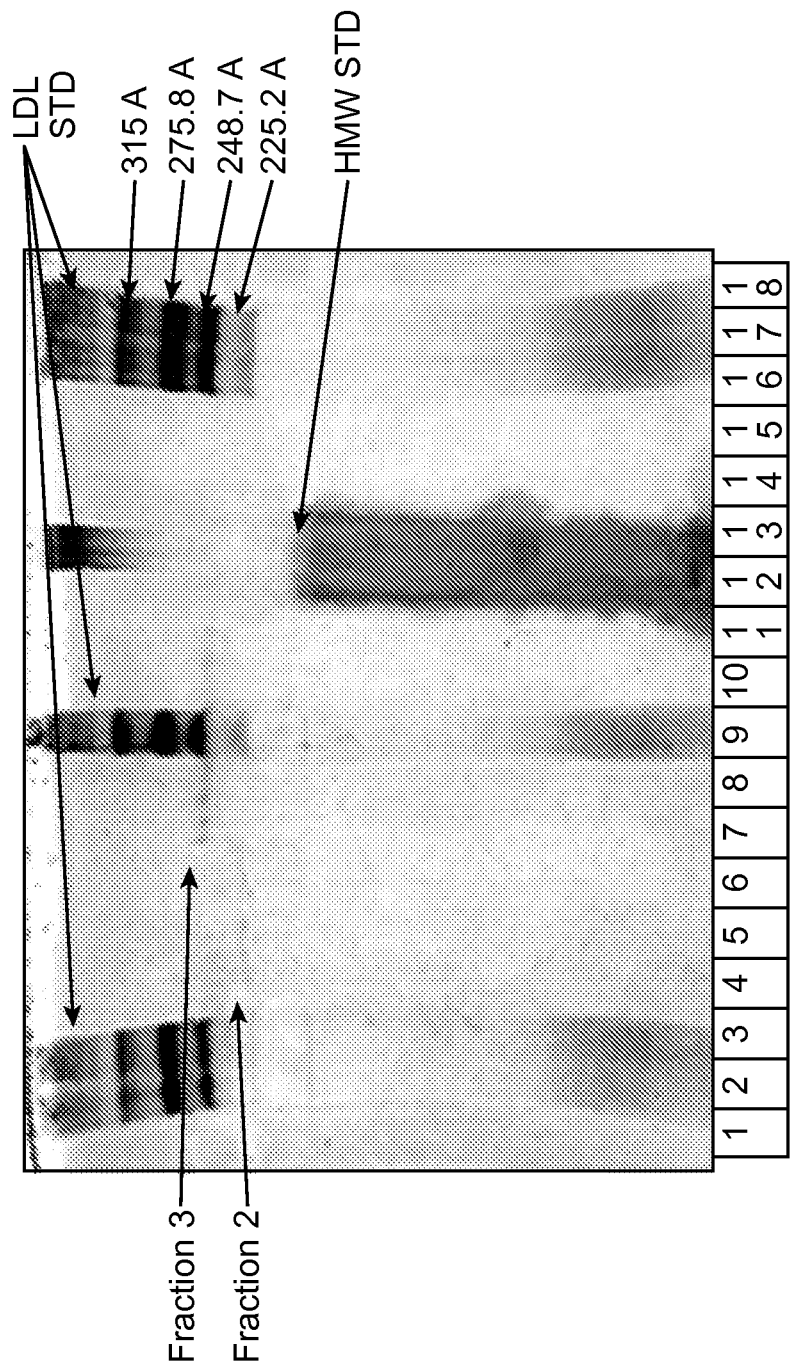
FIG. 8 depicts the results of 2-14% gradient gel electrophoresis (GGE), followed by lipid staining with Sudan Black, of fractions 2 and 3 described in FIGS. 6 and 7. Lanes 1, 2, 8, 17 & 18, lipoprotein standards; lanes 3-5, fraction 2; lanes 6 & 7, fraction 3; lanes 9-12, empty; lane 13, high molecular weight protein standards; lanes 14-16, empty.

FIG. 8 depicts the results of 2-14% gradient gel electrophoresis (GGE), followed by lipid staining with Sudan Black, of fractions 2 and 3 described in FIGS. 6 and 7. Lanes 1, 2, 8, 17 & 18, lipoprotein standards; lanes 3-5, fraction 2; lanes 6 & 7, fraction 3; lanes 9-12, empty; lane 13, high molecular weight protein standards; lanes 14-16, empty.

Figure 9:
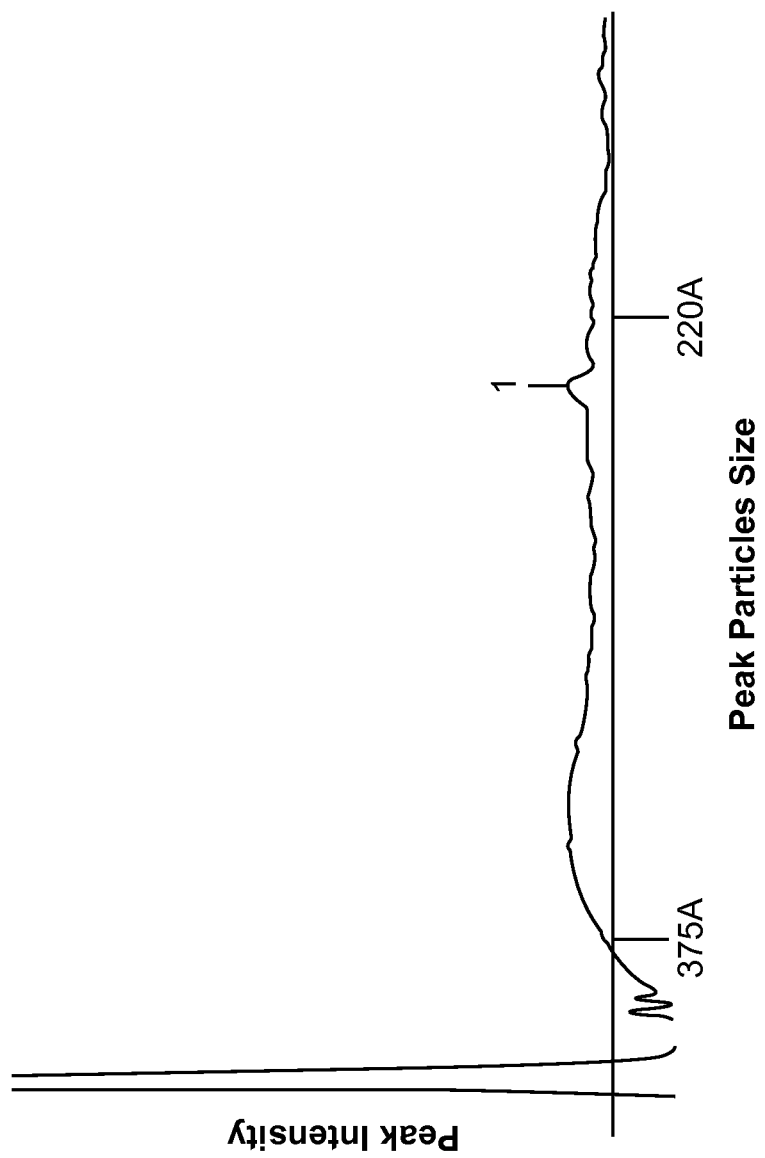
FIG. 9 depicts the densitometric scan of lane 3 in FIG. 8.

FIG. 9 depicts the densitometric scan of lane 3 in FIG. 8.

Figure 10:
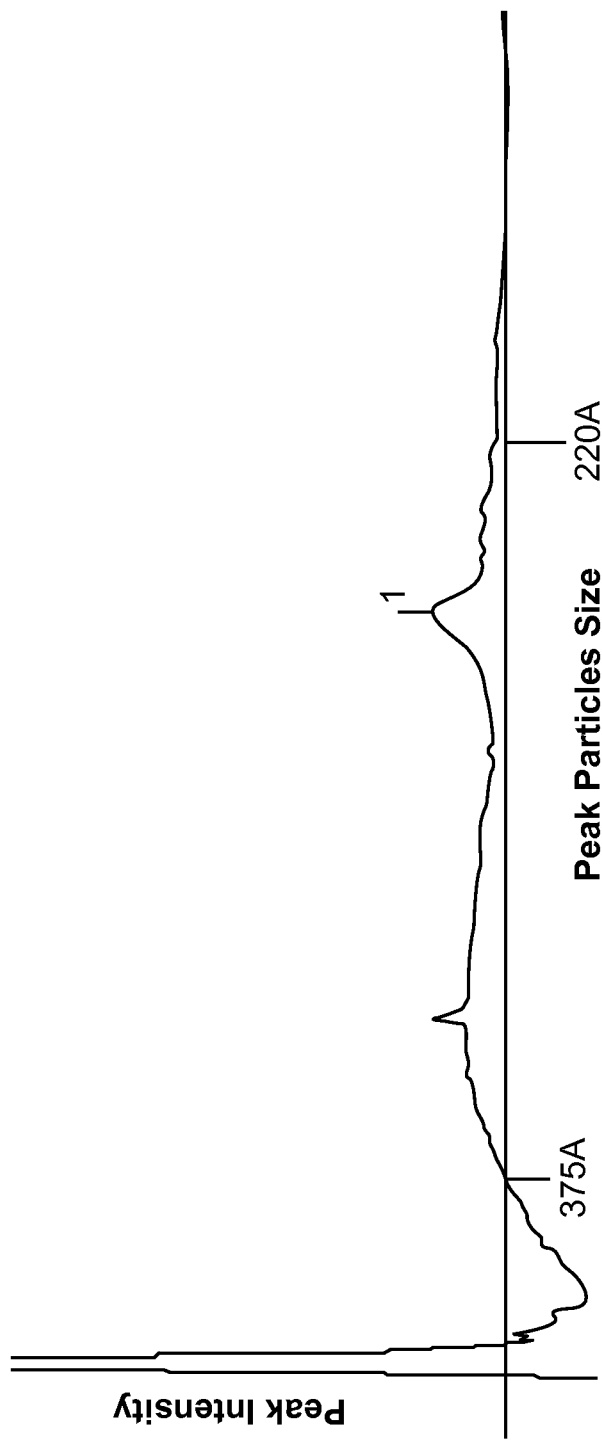
FIG. 10 depicts the densitometric scan of lane 4 in FIG. 8.

FIG. 10 depicts the densitometric scan of lane 4 in FIG. 8.

Figure 11:
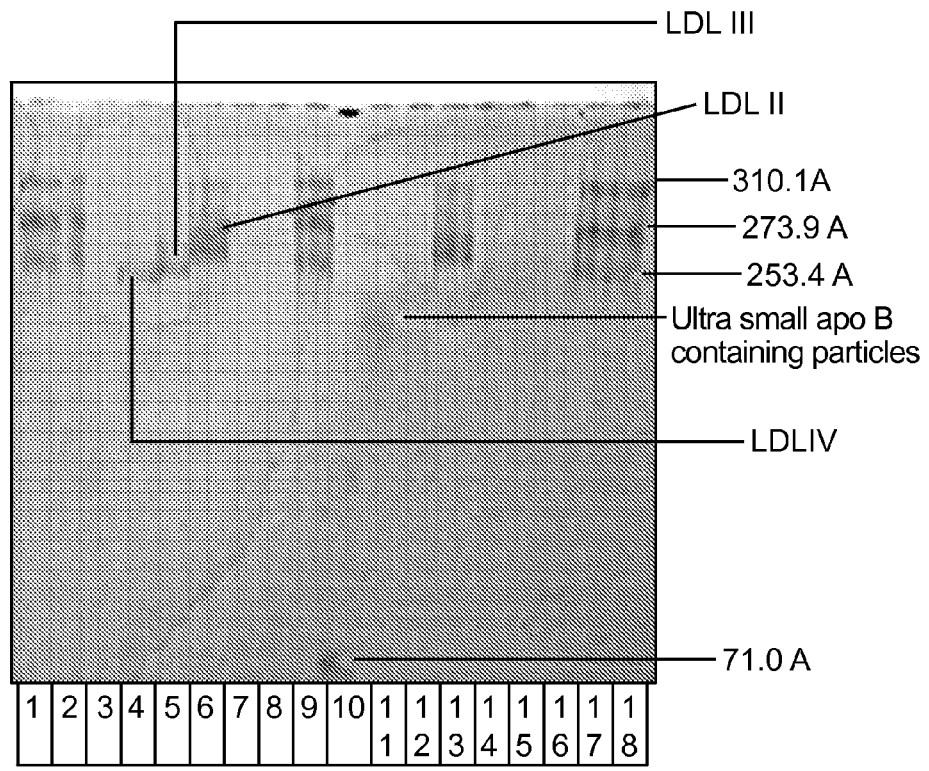
FIG. 11 depicts a 2-14% GGE stained with Coomassie blue of fractions 1, 2 and 3 from the elution window shown in FIG. 4. Lanes 1, 2, 9, 17 & 18, lipoprotein standards; lanes 4-6, fraction 2, 3 and 4; lanes 3, 7, 8, 15 and 16, empty; lane 10, bovine serum albumin; lane 13, LDL control; lanes 11, 12 and 14, ultra small apo B containing particles.

FIG. 11 depicts a 2-14% GGE stained with Coomassie blue of fractions 1, 2 and 3 from the elution window shown in FIG. 4. Lanes 1, 2, 9, 17 & 18, lipoprotein standards; lanes 4-6, fraction 2, 3 and 4; lanes 3, 7, 8, 15 and 16, empty; lane 10, bovine serum albumin; lane 13, LDL control; lanes 11, 12 and 14, ultra small apo B containing particles.

Figure 12:
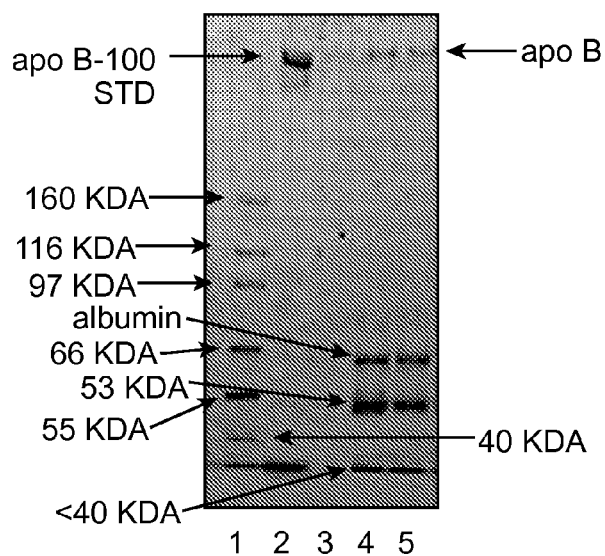
FIG. 12 depicts a sodium dodecyl sulfate (SDS) polyacrylamide of fraction 1 from the elution window shown in FIG. 4. Lane 1, molecular weight standard, lane 2, apo B-100 control, lane 3 empty; lane 4 and 5, ultra small apo B containing particles.

FIG. 12 depicts a sodium dodecyl sulfate (SDS) polyacrylamide of fraction 1 from the elution window shown in FIG. 4. Lane 1, molecular weight standard, lane 2, apo B-100 control, lane 3 empty; lane 4 and 5, ultra small apo B containing particles.

Western Immunoblotting for apoB-100 Identification

Figure 13:
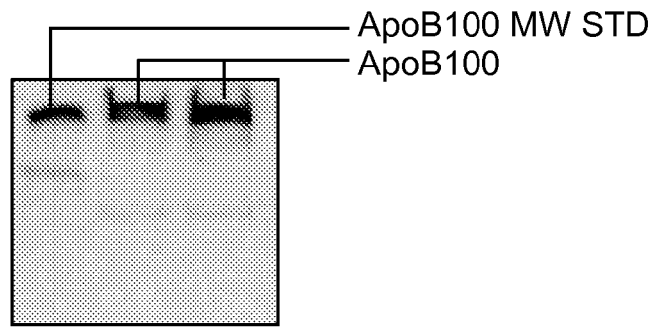
FIG. 13 depicts apoB-100 immunoblotting of fraction 1 samples derived from two individuals (lanes 2 and 3)
Figure 14:
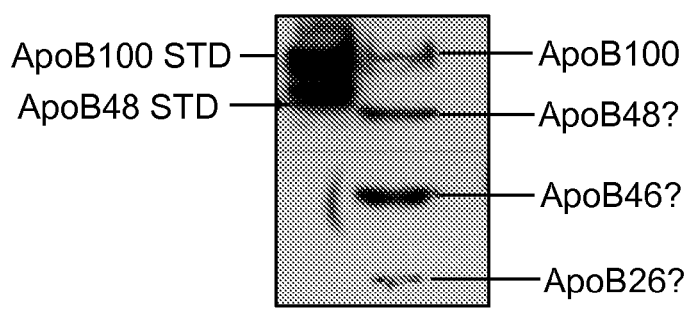
FIG. 14 depicts apoB-100 immunoblotting of fraction 1 samples derived from a third individual.

FIG. 13 depicts apoB-100 immunoblotting of fraction 1 samples derived from two individuals (lanes 2 and 3), FIG. 14 depicts apoB-100 immunoblotting of fraction 1 samples derived from a third individual.

Cytokeratin 8

Figure 15:
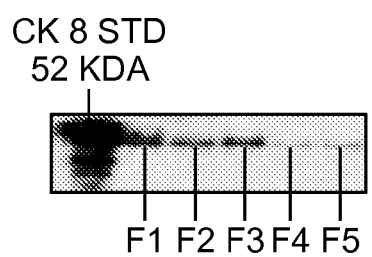
FIG. 15 depicts cytokeratin 8 (CK8) immunoblotting of fractions 1-5 (F1 to F5) isolated from a single individual using the elution window described in FIG. 4. First left lane, CK standard; lanes F1 to F5, fractions 1 to 5.

The specific antibody against cytokeratin "8" reacted, to a variable extent, with ≈53 KDA protein band blotted from the very high density, ultra small, lipid depleted apo B containing particles (F1), LDL-IV (F2), LDL-III (F3) and Lp(a), but not with LDL-II (F4) and LDL-I (F5) fractions eluted with GGE method and separated on SDS-PAGE (FIG. 15). Cytokeratin "8" was blotted from the 53 kDa bands of the very high density, ultra small, lipid depleted apo B containing particles eluted from 5 different plasma samples, and against the whole plasma. The first two subjects on the left side in FIG. 16 were recognized as LDL subclass pattern 'B' with predominantly small dense LDL, while the other three subjects were pattern 'A'. In the whole plasma sample, the cytokeratin "8" antibody reacted with the proteins corresponding to cytokeratin "8" in terms of its molecular weight and the molecular weight standard (STD), in addition to the presence of some other bands on the same, whole plasma lane. The appearance of the other additional bands may have been due to non-specific binding or to the presence of other cytokeratins with a homologous peptide sequence to cytokeratin "8".

FIG. 15 depicts cytokeratin 8 (CK8) immunoblotting of fractions 1-5 (F1 to F5) isolated from a single individual using the elution window described in FIG. 4. First left lane, CK standard; lanes F1 to F5, fractions 1 to 5.

Figure 16:
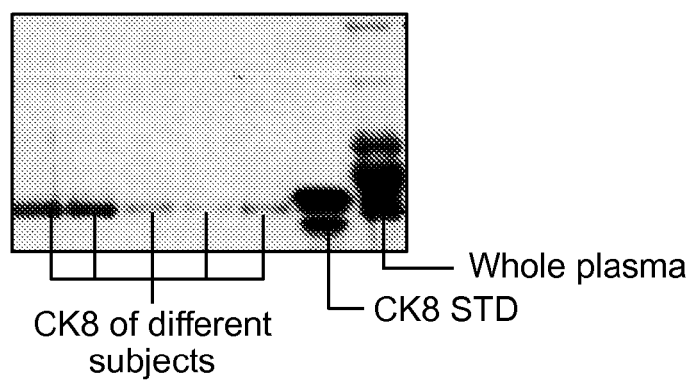
FIG. 16 depicts cytokeratin 8 immunoblotting of fraction 1 isolated from 5 individuals as described in FIG. 4.

FIG. 16 depicts cytokeratin 8 immunoblotting of fraction 1 isolated from 5 individuals as described in FIG. 4. Additionally, the CK "8" antibody was tested against whole plasma. The first two subjects on the left side are recognized as having LDL subclass pattern B, with respect to the distribution of their LDL particles.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of analyzing a biological sample obtained from an individual, the method comprising:

isolating from the sample a very high density, ultra small, lipid-depleted particle comprising apolipoprotein B (apoB), wherein the isolated particle has an average particle diameter in a range of from about 7.1 nm to about 22 nm, has a density >1.21 g/mL, and has substantially no cholesterol and substantially no triglyceride; and detecting a level of the isolated particle, wherein a level of the particle that is higher than a normal control level indicates that the individual has an increased risk of CVD) and/or that the individual has an increased risk of mortality due to a CVD.

2. The method of claim 1, wherein the biological sample is blood or a blood fraction.

3. The method of claim 1, further comprising generating a report that provides an indication of the risk that the individual will develop CVD.

4. The method of claim 1, wherein the individual is a human.

5. The method of claim 1, wherein the individual exhibits at least one clinical symptom or sign of cardiovascular disease.

6. The method of claim 1, further comprising communicating to the individual various treatment options based on the results of the detecting step.

7. The method of claim 1, further comprising treating the individual for CVD.

8. The method of claim 1, wherein the individual is an individual receiving a treatment for a cardiovascular disease, and the sample comprises a pre-treatment sample and a post-treatment sample, and the detecting step comprises detecting a post-treatment level of the isolated particle and a pre-treatment level of the isolated particle, wherein a post-treatment level that is lower than the pre-treatment level indicates that the treatment was efficacious.

9. The method of claim 8, wherein the individual is a human.

10. The method of claim 1, wherein the isolating step comprises subjecting the sample comprising the particle to:
(i) an immunoaffinity method; and collecting a fraction binding to an antibody specific to apoB in the immunoaffinity method;
(ii) a density gradient method; and collecting a fraction having a density >1.21 g/mL in the density gradient method; or
(iii) a gradient gel electrophoresis method; and collecting a fraction advancing beyond an LDL IV standard in the gradient gel electrophoresis method.

11. The method of claim 10, wherein the subjecting step comprises:
subjecting the sample comprising the particle to the gradient gel electrophoresis method; and
collecting the fraction advancing beyond the LDL IV standard.

12. The method of claim 1, wherein the detecting comprises contacting the isolated particle with a detectable antibody that binds apolipoprotein B-100.

13. The method of claim 1, wherein the method further comprises:
assessing the risk of CVD or mortality due to CVD for the individual based on the individual's detected level of the particle; and
communicating to the individual the assessment of the risk and/or a suggested treatment regimen for CVD.

14. The method of claim 1, wherein the method further comprises:
assessing the risk of CVD or mortality due to CVD for the individual based on the individual's detected level of the particle; and
generating a report that comprises the assessment of the risk, and the detected and control levels of the particle.

15. A method of isolating a very high density, ultra small, lipid-depleted particle, wherein the method comprises:
subjecting a sample comprising a very high density, ultra small, lipid-depleted particle comprising apoB to:
(i) an immunoaffinity method; and collecting a fraction binding to an antibody specific to apoB in the immunoaffinity method;
(ii) a density gradient method; and collecting a fraction having a density >1.21 g/mL in the density gradient method; or
(iii) a gradient gel electrophoresis method; and collecting a fraction advancing beyond a low density lipoprotein IV (LDL IV) standard in the gradient gel electrophoresis method,
thereby isolating the very high density, ultra small, lipid-depleted particle, wherein the particle has an average particle diameter in a range of from about 7.1 nm to about 22 nm, has a density >1.21 g/mL, and has substantially no cholesterol and substantially no triglyceride.

16. The method of claim 15, wherein the subjecting step comprises contacting a sample comprising the particle with an immobilized antibody specific for apoB; and eluting particles bound to the apoB.

17. The method of claim 15, wherein the apoB comprises an amino acid sequence having at least 95% amino acid sequence identity with the amino acid sequence set forth in SEQ ID NO:1.

18. The method of claim 15, wherein the isolated particle is at least 85% pure.

19. The method of claim 15, wherein the isolated particle is at least 95% pure.

20. A method of detecting a very high density, ultra small, lipid-depleted particle in a biological sample, wherein the particle comprises apoB, and wherein the particle has an average particle diameter in a range of from about 7.1 nm to about 22 nm, has a density >1.21 g/mL, and has substantially no cholesterol and substantially no triglyceride, the method comprising:
a) isolating the particle according to the method of claim 15 to obtain an enriched sample containing the isolated particles;
b) contacting the enriched sample with a detectable antibody that binds apolipoprotein B-100; and
c) detecting binding of the antibody to molecules in the enriched sample.

21. The method of claim 20, wherein the biological sample is obtained from an individual who is being evaluated for possible cardiovascular disease (CVD) or CVD risk.

22. The method of claim 20, wherein the detectable antibody comprises a detectable label.

23. The method of claim 22, wherein the detectable label is selected from the group consisting of: a magnetic bead, a fluorescent dye, a radiolabel, enzyme, a colloidal gold and a colored glass or plastic bead.

24. A kit for assessing risk of cardiovascular disease, the kit comprising:
a) a reagent that specifically binds apolipoprotein B-100; and
b) an isolated, very high density, ultra small, lipid-depleted particle comprising apolipoprotein B (apoB), wherein the isolated particle has an average particle diameter in a range of from about 7.1 nm to about 22 nm, has a density >1.21 g/mL, and has substantially no cholesterol and substantially no triglyceride.

25. The kit of claim 24, further comprising instructions for use.

26. The kit of claim 24, wherein each of (a) and (b) is in a separate container.

27. The kit of claim 24, wherein the reagent is an antibody, and wherein the antibody is immobilized on an insoluble support or is detectably labeled.

* * * * *